United States Patent
Saitoh et al.

(10) Patent No.: US 6,485,931 B2
(45) Date of Patent: Nov. 26, 2002

(54) CHOLESTEROL DEHYDROGENASE, COPROSTAN-3-ONE DEHYDROGENASE AND 4-CHOLESTEN-3-ONE DEHYDROGENASE, COMPOSITIONS CONTAINING THE DEHYDROGENASES, AND METHOD FOR REDUCING AMOUNT OF CHOLESTEROL USING THE COMPOSITIONS

(75) Inventors: Chiaki Saitoh, Ami-machi (JP); Hideyo Kumazawa, Machida (JP); Kazuo Aisaka, Machida (JP); Toru Mizukami, Machida (JP); Katsuhiko Ando, Machida (JP); Keiko Ochiai, Ebina (JP); Ryoichi Katsumata, Miyagi-ken (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/750,692

(22) Filed: Jan. 2, 2001

(65) Prior Publication Data

US 2001/0005587 A1 Jun. 28, 2001

Related U.S. Application Data

(62) Division of application No. 09/101,327, filed as application No. PCT/JP97/04067 on Nov. 7, 1997, now Pat. No. 6,312,919.

(30) Foreign Application Priority Data

Nov. 7, 1996 (JP) ............................. 8-294986

(51) Int. Cl.$^7$ ................................. C12P 1/04
(52) U.S. Cl. ....................................... 435/41
(58) Field of Search ......................... 435/170

(56) References Cited

U.S. PATENT DOCUMENTS

| | | |
|---|---|---|
| 4,921,710 A | 5/1990 | Beitz et al. |
| 5,436,004 A | 7/1995 | Beitz et al. |
| 5,503,988 A | 4/1996 | Saito et al. ............ 435/22 |

FOREIGN PATENT DOCUMENTS

| | | |
|---|---|---|
| DE | 2305232 | 8/1974 |
| EP | 1237483 | 6/1971 |
| GB | 1412244 | 10/1975 |
| JP | 58-89200 | 5/1983 |
| JP | 63-267231 | 11/1988 |
| JP | 218064 | 4/1990 |
| JP | 576311 | 3/1993 |
| WO | 93/25702 | 12/1993 |

OTHER PUBLICATIONS

Dehal et al., "A Novel Method to Decrease the Cholesterol Content of Foods" (1991) Adv. Appl. Biotechnol. Ser., vol. 12 (Fat Cholesterol Reduced Foods), pp. 203–220.*
Mott et al., "Plasmenylethanolamine: Growth Factor for Cholesterol Reducing Eubacterium" (1979) Journal Bacteriol., 139(3), 755–760.*
Mott et al., "Biochemical Characterization of Cholesterol–Reducing Eubacterium" (1980) Appl. Environ. Microbiol., 40(6), 1017–1022.*
Brinkley et al., "Isolation and Characterization of New Strains of Cholesterol–Reducing Bacteria from Baboons" (1982) Appl. Environ. Microbiol., 43,(1), 86–89.*
Sadzikowski et al., "Cholesterol–Reducing Bacterium from Human Feces" (1977) Appl. Environ. Microbiol., 34(4), 355–362.*
Ren, et al., "Mechanism of Cholesterol Reduction to Coprostanol by Eubacterium coprostanoligenes ATCC 51222", Steroids, vol. 61 (Jan. 1996), pp. 33–40.
Eyssen, et al., "Biohydrogenation of Sterols by Eubacterium ATCC 21,408–Nova Species", Eur. J. Biochem., vol. 36 (1973), pp. 411–421.
Faseb, J., vol. 6, No. 5 (1992) D. Ren et al., "Mechanism of cholesterol conversion to coprostanol by Eubacteria sp.HL", p. A1669.
Current Microbiology, vol. 30, No. 5 (1995), D.H. Mallonee et al., "Expression in *Escherichia coli* and characterization of bile acid–inducible 3α–hydroxysteroid dehydrogenase from Eubacterium sp. strain VP112708", p. 259–263.
Parmentier, et al., Mechanism of Biohydrogenation of Cholesterol to Coprostandol by Eubacterium ATCC 21 408, *Biochimica et biophysica Acta*, 348 (1974) 279–284.
A Resting Cell assay for Cholesterol Reductase Activity in Eubacterium Coprostanoligenes, ATCC 51222, Appl Microbiol Biotechnol (1995) 43:887–892, Li et al.
Eur. J. Biochem. 37, 143–147 (1973) "Microbial Transformation of Cholesterol into Coprostanol Properties of a 3–Oxo. . . " Björkhem et al.
"Studies on Nucleotide Metabolism in Porcine Longissimus Muscle Postmortem", pp. 612–616, Journal of Food Science, vol. 37 (1972) Tsai et al.
Archives of Biochemistry and Biophysics, 156, 143–153 (1973) Bernofsky et al.
Lett. Appl Microbiol Biotechnol (1992) 37:330–334, Somkuti et al.
Appl Microbiology (1995), 20:137–140, Bukman et al.
Differences in uptake and esterification of saturated analogues of cholesterol by rat small intestine, by A. Bhattacharyya; (1986) pp. G495–G500, Am. Jo. Physiol., vol. 251.

* cited by examiner

Primary Examiner—Jon P. Weber
(74) Attorney, Agent, or Firm—Antonelli, Terry, Stout & Kraus, LLP

(57) ABSTRACT

According to the present invention, a process for producing a practical cholesterol-reduced substance by converting cholesterol contained in foods and feeds to coprostanol having very low intestinal tract absorbability by utilizing enzymatic action is provided.

Cholesterol in a cholesterol-containing substance such as meat, egg, milk, seafood and cooked processed foods containing the same, or feeds for animals, poultry and pisciculture, and the like, can be treated with three kinds of enzymes which are a cholesterol dehydrogenase having an optimum pH in a neutral pH range and 4-cholesten-3-one dehydrogenase and coprostan-3-one dehydrogenase each having an optimum pH in a weak acidic range, or microbial cells containing the enzymes, for converting the cholesterol to coprostanol to reduce the amount of the cholesterol.

6 Claims, 6 Drawing Sheets

CHOLESTEROL DEHYDROGENASE, COPROSTAN-3-ONE DEHYDROGENASE AND 4-CHOLESTEN-3-ONE DEHYDROGENASE, COMPOSITIONS CONTAINING THE DEHYDROGENASES, AND METHOD FOR REDUCING AMOUNT OF CHOLESTEROL USING THE COMPOSITIONS

This application is a Divisional application of application Ser. No. 09/101,327, filed Jul. 7, 1998, now U.S. Pat. No. 6,312,919, which is an application filed under 35 USC 371 of PCT/JP97/04067, filed Nov. 7, 1997.

TECHNICAL FIELD

The present invention relates to a method for producing a cholesterol-reduced substance, a cholesterol-reducing composition and a novel cholesterol dehydrogenase, 4-cholesten-3-one dehydrogenase and coprostane-3-one dehydrogenase for using the above-mentioned purpose.

BACKGROUND ART

It is widely known that excess intake of food having high cholesterol content increases the amount of cholesterol in serum and that high cholesterol content in serum is a significant factor in heart diseases. Therefore, processing techniques are required for selectively reducing the amount of cholesterol in food without deteriorating the quality of the food.

Among techniques for reducing the amount of cholesterol in food, a method is known that decomposes cholesterol with microorganisms (Japanese Laid-Open Patent Publication No. 267231/88) as a biochemical technique; however, this method produces by-products, therefore, it is not a safe method. Further, a method in which cholesterol is converted to epicholesterol by using an enzyme is known (WO93/25702).

Beitz, et al., U.S. Pat. No. 4,921,710 describes a method for converting cholesterol to coprostanol by using a cholesterol reductase derived from plants, and suggests a method for converting cholesterol to coprostanol by using a cholesterol reductase derived from bacteria such as *Eubacterium* species ATCC 21408. Also, Beitz, et al., U.S. Pat. No. 5,436,004 describes that the conversion ratio from cholesterol to coprostanol as 0.01% when a cream is treated using the above-mentioned enzyme derived from plants (see, column 5, table 1). However, such a low conversion ratio to coprostanol can not be admitted as practical level.

EYSSEN, British patent 1237483 describes that *Eubacterium* species bacterium separated from feces of rats reduces cholesterol to coprostanol, and also, in EYSSEN, Biochemica et Biophysica Acta, 348,279–284 (1974), it is estimated that the bacterium reduces cholesterol to coprostanol via 4-cholesten-3-one.

Beitz, et al., Applied Microbiology and Biotechnology 43, 887 (1995) describes that *Eubacterium* species bacterium (ATCC 51222) converts cholesterol in micelle to coprostanol, that 4-cholesten-3-one and trace amounts of coprostane have been detected in the conversion process, and that the reduction mechanism of cholesterol using the above-mentioned bacterium might be studied after pure preparations of the cholesterol reductase are obtained.

However, up to now, it has not been confirmed that cholesterol in a substance containing cholesterol is converted via 4-cholesten-3-one and coprostane-3-one to coprostanol by utilizing enzymatic action of cholesterol dehydrogenase, 4-cholesten-3-one dehydrogenase, coprostane-3-on dehydrogenase with using a coenzyme AND (P) and AND (P) H, and enzymes which convert cholesterol in a substance containing cholesterol to coprostanol via 4-cholesten-3-one and coprostane-3-one, respectively, have not been isolated from bacterium which reduces cholesterol, and in addition, no report have been proposed in which food is treated with these converting enzymes and microorganism containing the same.

It is known that cholesterol dehydrogenase derived from *Nocardia, Alcaligenes, Proteus,* which has optimum pH of around 9.0, requires AND (P) as a coenzyme, and is used for a quantitative determination of cholesterol (Japanese Post-Examined Patent Publication No.18064/90), however, this enzyme exhibits low activity at neutral pH, so that it can not be admitted as practical for food treatment.

Testing has been tried to obtain 4-cholesten-3-one dehydrogenase from the feces of a rat, however, the dehydrogenase is rapidly deactivated and can not be purified in this method, therefore, the method can not be admitted as practical (European J. of Biochemistry 37, 143 (1973)).

It is known that treatment of food with a phospholipase, protease and lipase accelerates conversion by a cholesterol oxidase (Japanese Laid-Open Patent publication No.76311/93), however, effect in enzymatic conversion of cholesterol to coprostanol is not known yet.

It is known that meat contains AND (H) (Journal of Food Science 37, 612 (1972)), and that nicotinamide inhibits decomposition of AND (Archives of Biochemistry and Biophisics 156, 143 (1973)). However, addition of nicotinamide in enzymatically converting cholesterol to coprostanol is not known.

It is known that an introduction of the cholesterol oxidase gene into lactic acid bacteria for decomposing food cholesterol (Applied Microbiology and Biotechnology 37, 330 (1992)).

As an applied example of these enzymes, the above-mentioned Beitz, et al., U.S. Pat. No. 5,436,004 suggests a treating method for reducing the amount of cholesterol in serum in which a cholesterol reductase derived from plants is orally administered. Further, it is reported that if a bacterium (ATCC 51222) which reduces cholesterol is orally administered to a rabbit suffering from hypercholesterolemia, the cholesterol level in serum decreases (Letters in Applied Microbiology 20, 137 (1995)).

Since absorbability of coprostanol through the intestinal tract is very low (American J. of Physiology 251, G495 (1986)), conversion of cholesterol to coprostanol is effective as a cholesterol reducing method. A practical method is not known for producing a cholesterol-reduced substance which reduces cholesterol by enzymatically converting cholesterol in food via 4-cholesten-3-one and coprostane-3-one to coprostanol. Also, a method for producing a practical enzyme which can be used in the above-mentioned production method is not known.

DISCLOSURE OF THE INVENTION

The object of the present invention is to provide a novel method for producing a practical cholesterol-reduced substance in food and feed. Another object of the present invention is to provide a novel cholesterol dehydrogenase having optimum pH in neutral pH range which is suitable for the above-mentioned practical method for producing a cholesterol-reduced substance, a novel 4-cholesten-3-one dehydrogenase and coprostane-3-one dehydrogenase having an optimum pH in a weak acidic pH range possessed by meat, and microbial cells and a treated material thereof containing these enzymes. A further object of the present invention is to provide a cholesterol-reducing composition which reduces cholesterol level in serum, comprising the above-mentioned three kinds of novel enzymes or comprising microbial cells containing these novel enzymes.

The present inventors have screened various microorganisms such as stock microorganisms mainly including 300 kinds (species categories) of actinomycetes, fungi and bacteria, aerobic bacteria separated from 100 kinds of various soils, and anaerobic bacteria from 7 feces samples of humans, 8 feces samples of mammals other than human and 9 feces samples of birds, to find a cholesterol reduction converting enzyme group having optimum pH in a neutral pH range or weak acidic range for solving the above-mentioned problems, and have intensively examined a culture medium for enzymatic activity detection and a method for recovering microbial cells, as a result, have accomplished the present invention.

Namely, the present invention relates to a process for producing a cholesterol-reduced substance and a method for reducing the amount of cholesterol, wherein cholesterol in a substance containing cholesterol such as meat, egg, milk, seafood and cooked processed food containing the same, or feed for animals, poultry and pisciculture, and the like, is treated with three kinds of enzymes consisting of cholesterol dehydrogenase having optimum pH in neutral pH range and 4-cholesten-3-one dehydrogenase and coprostan-3-one dehydrogenase having optimum pH in a weak acidic range or microbial cells containing these enzymes, to convert cholesterol to coprostanol for reducing the amount of cholesterol.

Further, the present invention relates to the above-mentioned three kinds of enzymes consisting of cholesterol dehydrogenase having optimum pH in a neutral pH range and 4-cholesten-3-one dehydrogenase and coprostan-3-one dehydrogenase having optimum pH in weak acidic range, produced by a strain belonging to *Eubacterium*, a cholesterol-reducing composition comprising these three kinds of enzymes, and a cholesterol-reducing composition comprising a strain belonging to *Eubacterium* which produce this enzyme group.

Further, the present invention relates to a process for producing a cholesterol-reduced substance and a method for reducing the amount of cholesterol wherein nicotinamide, phospholipase and nicotinamide, or a phosphate ion are added when cholesterol in a cholesterol-containing substance is converted to coprostanol by utilizing the above-mentioned enzyme group.

The process for producing a cholesterol-reduced substance of the present invention will be described in detail below.

In the present invention, examples of the cholesterol-containing substance include meat, egg, milk, seafood and cooked processed foods containing the same, or feeds for animals, poultry and pisciculture, and the like, but are not limited to them providing the substance containing cholesterol.

In the present invention, the cholesterol dehydrogenase is an enzyme conducting the following reaction.

Cholesterol+AND(P) →4-cholesten-3-one+AND(P)H

Further, in the present invention, the 4-cholesten-3-one dehydrogenase is an enzyme conducting the following reaction.

Similarly, in the present invention, the coprostan-3-one dehydrogenase is an enzyme conducting the following reaction.

Coprostan-3-one+AND(P)H→coprostanol+AND(P)

In the present invention, the term "optimum pH" refers to a pH range in which relative active value is not less than 80% of the maximum active value, and the case in which pH 7.0 is included in such a pH range is referred to as "having optimum pH in a neutral pH range" in the present invention.

Similarly, the phrase "having optimum pH in a weak acidic range" in the present invention refers to a case in which pH 5.5 is included in the optimum pH range and the maximum active value exists in the acidic side.

For converting cholesterol in a cholesterol-containing substance to coprostanol via 4-cholesten-3-one and coprostan-3-one by utilizing the enzymatic actions of cholesterol dehydrogenase, 4-cholesten-3-one dehydrogenase and coprostan-3-one dehydrogenase sequentially in the present invention, any of an enzymatic conversion method using these enzymes and a microbial conversion method using microbial cells having these enzymatic activities can be used.

As the enzymatic conversion method, there is listed, for example, a method in which enzymes having activities of the above-mentioned cholesterol dehydrogenase, 4-cholesten-3-one dehydrogenase and coprostan-3-one dehydrogenase are added to a cholesterol-containing substance for converting cholesterol to coprostanol, and the enzyme which can be used in this enzymatic conversion method is not limited to a purified enzyme and may also be a crude enzyme which has not been purified but has enzymatic activity.

It is particularly desirable in this enzymatic conversion method to be sequentially treated with cholesterol dehydrogenase, the treatment with 4-cholesten-3-one dehydrogenase and the treatment with coprostan-3-one dehydrogenase continuously by successively-adding the enzymes and the like, from practical points of view such as simplification of the enzyme treatment process, improvement of conversion rate, and the like.

As the above-mentioned microbial conversion method, there is listed a method in which microbial cells having at least one enzymatic activity of cholesterol dehydrogenase activity, 4-cholesten-3-one dehydrogenase activity and coprostan-3-one dehydrogenase activity, or a treated material thereof are added to a cholesterol-containing substance for converting cholesterol to coprostanol, and it is desirable to use microbial cells having these enzymatic activities simultaneously or a treated material thereof. Further, a recombinant microbial cells having these enzymatic activities or a treated material thereof can also be used.

The material having the above-mentioned enzymatic activity (hereinafter, referred to as "enzyme source") is usually added in the form of a powder or aqueous solution to a cholesterol-containing substance. Further, if necessary, coenzymes such as AND (P), AND (P) H and the like, enzymes such as phospholipase, lipase, protease and the like, or nicotinamide, phosphate ion and the like can be used alone or in combination together with the enzyme source.

In treatment for meat, for example, beef, pork, mutton or chicken, the enzyme source is mixed with minced meat, dispersed in sliced meat or injected in block meat. Further, the enzyme source can also be injected in blood vessels before and after slaughtering.

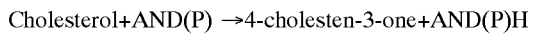

In treatment for milk, the enzyme source is added to milk, or milk is passed through a carrier to which the enzyme source is fixed. Further, in the case of fermented milk food, the enzyme source can also be added at milk fermentation.

In the treatment for eggs, the enzyme source is injected in the whole egg, or the enzyme source is mixed with yolk obtained by cracking the egg.

Further, when meat, milk, egg or seafood is cooked, the enzyme source may be added.

Regarding feeds for animals, poultry and pisciculture, it is possible to use a raw material for feed which has been treated with the enzyme source, or to mix the enzyme source in the process for preparing a feed.

In the above-mentioned enzymatic treatment, treatment conditions (temperature, time, pH) and the amount of enzyme to be added under which enzymatic conversion to coprostanol is possible are selected, and in general, the treatment is conducted at reaction temperature of 2 to 70° C. and pH of 4 to 9 for 0.5 to $1 \times 10^3$ hours, and it is desirable to used a cholesterol reductase having optimum pH in the pH range possessed by the cholesterol-containing food itself to be treated in a practical point of view.

The amount used of each enzyme which is cholesterol dehydrogenase, 4-cholesten-3-one dehydrogenase or coprostan-3-one dehydrogenase to be used is from 1 to $1 \times 10^5$ units, preferably from $1 \times 10^2$ to $1 \times 10^4$ units per gram of cholesterol in food.

Optionally, AND(P) or AND(P)H which is a coenzyme of the above-mentioned enzyme can be added in an amount of $1 \times 10^{-4}$ to $2 \times 10^2$ g per gram of cholesterol.

Optionally, nicotinamide can also be added in an amount from 0.01 to 5% in terms of concentration in food. In meat which exhibits strong activity of decomposing these coenzymes it is preferable to added nicotinamide in an amount of 0.1% or more.

If required, a phosphate ion can also be added in an amount from 5 to 25 mM.

If occasion requires, it is also possible to add a phospholipase in an amount from 1 to $1 \times 10^5$ units per gram of a phospholipid and to add a lipase in an amount from 1 to $1 \times 10^5$ units per gram of a lipid.

Specific examples of the novel enzymes of the present invention include cholesterol dehydrogenase A, 4-cholesten-3-one dehydrogenase A and coprostan-3-one dehydrogenase A, cholesterol dehydrogenase B, 4-cholesten-3-one dehydrogenase B and coprostan-3-one dehydrogenase B. The method for production and the physical and chemical properties of these enzymes are described below.

The microorganism used in producing the novel cholesterol dehydrogenase A, 4-cholesten-3-one dehydrogenase A and coprostan-3-one dehydrogenase A may be any microorganism having ability to produce the above-mentioned cholesterol dehydrogenase A, 4-cholesten-3-one dehydrogenase A and coprostan-3-one dehydrogenase A, and may also be a variant species or variant strain thereof. As a specific example of the microorganism having ability to produce the cholesterol dehydrogenase A, 4-cholesten-3-one dehydrogenase A and coprostan-3-one dehydrogenase A, for example, *Eubacterium* sp. CP 2 is listed.

The above-mentioned *Eubacterium* sp. CP 2 is a strain which has been newly separated from the feces of lions by the present inventors, and mycological properties thereof are as follows.

The present strain exhibits excellent growth by standing culture in a solution under anaerobic conditions at 37° C. using the following basal medium. Tests regarding various properties were investigated under this condition.

Basal medium; 1% Casitone, 1% yeast extract, 0.5% soluble starch, 0.5% sodium pyruvate, 0.05% sodium thioglycolate, 0.05% calcium chloride, 0.0001% Resazurin, and 0.01% lecithin (pH 7.5)

(a) Morphological properties
① Form of cell; short rod bacterium, and sometimes shown as almond figure.
② Size of cell; 0.5 to 0.7 μm×0.7 to 1.0 μm
③ Polymorphism; none
④ Mobility; none
⑤ spore; none (b) Cultural properties No growth was observed in bouillon plate agar-media and bouillon broth medium under aerobic or anaerobic conditions.

Cultural properties under a culturing condition and basal medium in which the present strain can grow are shown below.

① Basal medium agar plate culture (culturing for 14 days)
  i) Appearance of growth; forming weak small colony
  ii) Color; transparent white
  iii) Gloss; recognized
  iv) Dispersible pigment; none
② Basal medium solution culture (culturing for 3 days)
  i) Growth on surface; none
  ii) Turbidity; grown in the form of white emulsion at the bottom part
③ Gelatin stab culture in Basal medium
  i) Condition of growth; excellent
  ii) Liquefaction of gelatin; none (c) Physiological properties in basal medium culture
① Gram staining; positive
② Reduction of nitrate; negative
③ Denitrification reaction; negative
④ MR test; negative
⑤ DVP test; negative
⑥ Generation of indole; negative
⑦ Generation of hydrogen sulfide; positive
⑧ Hydrolysis of starch; negative
⑨ Decomposition of esculin; positive
⑩ Utilization of an inorganic nitrogen source in a medium which has been obtained by removing 1% casitone and 1% yeast extract from the basal medium
  i) Nitrate; negative
  ii) Ammonium salt; negative
⑪ Generation of pigment; none
⑫ Urease; negative
⑬ Oxidase; negative
⑭ Catalase; negative
⑮ Growth range
  i) Growth pH range; pH 6.0 to pH 7.7 (optimum growth; around pH 7.3)
  ii) Growth temperature range; 28 to 44° C. (optimum growth temperature; around 35° C.)
⑯ Attitude against oxygen; strictly anaerobic
⑰ O-F test (Hugh Leifson method); negative
⑱ Generation of acid and gas
  i) L-arabinose; acid (none), gas (none)
  ii) D-xylose; acid (none), gas (none)

iii) D-glucose; acid (observed), gas (none)
iv) D-mannose; acid (observed), gas (none)
v) D-fructose; acid (none), gas (none)
vi) D-galactose; acid (observed), gas (none)
vii) Maltose; acid (none), gas (none)
viii) Sucrose; acid (none), gas (none)
ix) Lactose; acid (none), gas (none)
x) Trehalose; acid (none), gas (none)
xi) D-sorbitol; acid (none), gas (none)
xii) D-mannitol; acid (none), gas (none)
xiii) Inositol; acid (none), gas (none)
xiv) Glycerin; acid (none), gas (none)
xv) Starch; acid (none), gas (none)
xvi) Metabolite from saccharides; butyric acid or acetic acid (d) Other various properties; test according to An-IDENT
① α-glucosidase; positive
② β-glucosidase; positive
③ Alkali phosphatase; positive
④ α-galactosidase; positive
⑤ Phenylalanineamino peptidase; negative
⑥ Decomposition of arginine; positive
⑦ Decomposition indoxyl acetate; negative The present strain was of a gram positive strictly anaerobic short rod bacterium, did not form a spore, had no mobility, was negative against all of a catalase, oxidase and urease and formed acids from glucose and lactose, and main metabolite thereof was butyric acid or acetic acid. The classificational position of the strain having these mycological properties was compared with the description of Bergey's Manual of Systematic Bacteriology vol. 2, 1986, as a result, the strain was identified as a bacterium belonging to *Eubacterium,* and the CP 2 strain was named as *Eubacterium* sp. CP 2. This strain was deposited in the name of FERM BP-5501 to National Institute of Bioscience and Human-Technology Agency of Industrial Science and Technology (Higashi 1-1-3, Tsukuba City, Ibaraki Prefecture, Japan) on Apr. 12, 1996.

As the medium used for culturing a microorganism which produces cholesterol dehydrogenase A, 4-cholesten-3-one dehydrogenase A and coprostan-3-one dehydrogenase A of the present invention, any of a synthetic medium or natural medium containing a carbon source, nitrogen source, inorganic substance and the like can be used.

As the carbon source, for example, various carbohydrates can be used such as a soluble starch, lactose, pyruvic acid, glucose, molasses and the like, and the amount used thereof is preferably from 1 to 20 g/L.

As the nitrogen source, for example, ammonium sulfate, ammonium phosphate, ammonium carbonate and ammonium acetate, or nitrogen-containing organic compounds such as peptone, yeast extract, corn steep liquor, casein decomposed material, meat extract, and the like, can be used, and the amount used thereof is preferably from 1 to 20 g/L.

As the inorganic substance, for example, sodium chloride, calcium chloride, magnesium sulfate and the like are used, and the amount used thereof is preferably from 0.1 to 2 g/L. The amount used of a surfactant such as lecithin and the like is preferably from 0.01 to 1 g/L. The amount used of sodium thioglycolate is preferably from 0.1 to 1 g/L.

Culturing is conducted under an anaerobic condition by standing culture or stirring culture. Culturing temperature may advantageously be a temperature at which a microorganism grows and produces cholesterol dehydrogenase A, 4-cholesten-3-one dehydrogenase A and coprostan-3-one dehydrogenase A, and preferably from 35 to 40° C. Culturing period varies depending on conditions, and culturing may advantageously be conducted until the maximum amount of cholesterol dehydrogenase A, 4-cholesten-3-one dehydrogenase A and coprostan-3-one dehydrogenase A are produced, and usually from about 5 to 10 days.

Cholesterol dehydrogenase A that is produced by the CP 2 strain is a novel enzyme, and the physical and chemical properties and method for purification thereof are as follows.
(a) Action: it catalyses the following reaction.
Cholesterol+NADP→4-cholesten-3-one+NADPH
(b) Substrate specificity The present enzyme reacts with steroid having a hydroxyl group at 3β position, and has relative activity of 38, 74, and 30 regarding β sitosterol, campesterol, stigmasterol when the activity of cholesterol is 100.
(c) Optimum pH: 6.5 to 7.8
(d) Stable pH: 5.3 to 9.0

An enzyme solution was allowed to stand still at 37° C. for 15 minutes using various pH buffer solutions, and remaining activity was measured, and pH range in which activity was not less than 50% of the maximum active value was regarded as a stable pH range. (The following is the same.)
(e) Measurement of titer:

With 0.2 ml of 3 mM cholesterol micelle solution containing 0.33% Triton X-100 is mixed 0.3 ml of a 20 mM piperazine-N,N'-bis-(2-ethane sulfuric acid) (hereinafter, referred to as "PIPES") buffer solution (pH 7.5) containing 0.5% Triton X-100 and 1 mM dithiothreitol (hereinafter, referred to as "DTT"), and 0.1 ml of a 10 mM AND solution, the resulted mixture is added 0.05 ml of an enzyme solution, reacted for 30 minutes at 37° C., and then added 0.1 ml of chloroform to extract sterol and to terminate the reaction.

Then, the quantity of 4-cholesten-3-one produced in the reaction solution is determined using TLC/FID iatroscan. The quantity of 4-cholesten-3-one produced in the reaction solution is determined likewise using an inactivated enzyme which has been previously heated as a control. The enzyme activity which produces 1 μmol of 4-cholesten-3-one per one minute is regarded as 1 unit.
(f) Range of suitable reaction temperature:

In reaction at pH 7.5 for 30 minutes, increasing temperature up to 40° C. is attended by increasing activity.
(g) Range of temperature stability After heating treatment at 40° C. for 10 minutes, it keeps activity of not less than 80% of that before the treatment.
(h) Influence of inhibitor, metal ion:

When 1 mM p-chloro mercury phenylsulfonate (PCMB), iodine acetamide and ethylenediamine tetraacetate (EDTA) are added and reacted for 30 minutes at pH 7.5 and 37° C., the relative activities are 0, 82 and 105 respectively, if the enzyme activity without adding inhibitor is defined as 100. Further, when the present enzyme is reacted in the presence of 1 mM iron chloride and copper chloride, the relative activities are 95 and 3.2, respectively, in comparison with the case of no addition.
(i) Purification method:

Microbial cells are collected from the culture by centrifugal separation, and the cells are suspended in a 20 mM PIPES buffer solution (pH 7.5, containing 1 mM MDTT). The cells are disrupted by ultrasonication, further, treated with ultrasonication in the presence of 0.2% Triton X-100, solid components are removed by centrifugal separation, to obtain a crude enzyme solution. The crude enzyme solution is dialyzed against a 20 mM PIPES buffer solution (pH 7.5, containing 1 mM DTT, 0.2% Triton X-100, 10% glycerol), then, adsorbed on Blue Sepharose CL-6B (Pharmacia) which has been equilibrated with the same buffer solution. Then, the above-mentioned buffer solution flows with sodium chloride concentration being increased continuously from 0 to 3.0 M, and active fractions are collected. The resulted active fractions are dialyzed against the same buffer solution, then, adsorbed on Red Sepharose CL-6B (Pharmacia). Then, the above-mentioned buffer solution flows with sodium chloride concentration being increased continuously from 0 to 3.0 M, and active fractions are collected to obtain a purified sample.

(j) Coenzyme:

β-nicotinamide adenine dinucleotide phosphoric acid (NADP) is used as a coenzyme.

(k) Molecular weight:

The molecular weight according to SDS polyacrylamide electrophoresis method is about 57,500.

The 4-cholesten-3-one dehydrogenase A of the present invention produced by the CP 2 strain is a novel enzyme, and the physical and chemical properties and method for purification thereof are as follows.

(a) Action: it catalyses the following reaction.

4-cholesten-3-one+NADH→coprostan-3-one+AND (b) Substrate specificity

The relative activities are 0, 41 and 0 for testosterone, progesterone and prognerone when the activity of 4-cholesten-3-one is defined as 100.

(c) Optimum pH: 5.4 to 6.5

(d) Stable pH: 5.5 to 7.2

(e) Measurement of titer:

With 0.2 ml of 3 mM 4-cholesten-3-one micelle solution containing 0.33% Triton X-100 is mixed 0.3 ml of a 20 mM PIPES buffer solution (pH 7.5) containing 0.5% Triton X-100 and 1 mM DTT, and 0.1 ml of a 10 mM NADH solution, the resulted mixture is added 0.05 ml of an enzyme solution, and reacted for 30 minutes at 37° C., and then added 0.1 ml of chloroform to extract sterol and to terminate the reaction.

Then, the quantity of coprostan-3-one produced in the reaction solution is determined using TLC/FID iatroscan. The quantity of coprostan-3-one produced in the reaction solution is determined likewise using an inactivated enzyme which has been previously heated as a control. The enzyme activity which produces 1 μmol of coprostan-3-one per one minute is regarded as 1 unit.

(f) Range of suitable reaction temperature:

In reaction at pH 6.0 for 30 minutes, increasing temperature up to 40° C. is attended by increasing the activity (g) Range of temperature stability After heating treatment at 40° C. for 10 minutes, it keeps activity of not less than 80% of that before the treatment.

(h) Influence of inhibitor, metal ion:

When 1 mM PCMB, iodine acetamide and EDTA are added and reacted for 30 minutes at pH 7.5 and 37° C., the relative activities are 47, 94 and 82 respectively, if the enzyme activity without adding inhibitor is defined as 100. Further, when the present enzyme is reacted in the presence of 1 mM iron chloride and copper chloride, the relative activities are 110 and 0, respectively, in comparison to the case of no addition.

(i) Purification method:

Microbial cells are collected from the culture by centrifugal separation, and the cells are suspended in a 20 mM PIPES buffer solution (pH 7.5, containing 1 mM MDTT). The cells are disrupted by ultrasonication, further, treated with ultrasonication in the presence of 0.2% Triton X-100, solid components are removed by centrifugal separation, to obtain a crude enzyme solution. The crude enzyme solution is dialyzed against a 20 mM PIPES buffer solution (pH 7.5, containing 1 mM DTT, 0.2% Triton X-100, 10% glycerol), then, adsorbed on Blue Sepharose CL-6B (Pharmacia) which has been equilibrated with the same buffer solution. Then, the above-mentioned buffer solution flows with sodium chloride concentration being increased continuously from 0 to 3.0 M, and active fractions are collected. The resulted active fractions are dialyzed against the same buffer solution, then, adsorbed on Resource Column (Pharmacia). Then, the above-mentioned buffer solution flows with sodium chloride concentration being increased continuously from 0 to 1.0 M, and active fractions are collected to obtain a purified sample.

(j) Coenzyme:

Reduced type β-nicotinamide adenine dinucleotide (NADH) is used as a coenzyme.

(k) Molecular weight:

The molecular weight according to SDS polyacrylamide electrophoresis method is about 37,500.

The coprostan-3-one dehydrogenase A of the present invention produced by the CP 2 strain is a novel enzyme, and the physical and chemical properties and method for purification thereof are as follows.

(a) Action: it catalyses the following reaction. coprostan-3-one+NADPH→coprostanol+NADP (b) Substrate specificity The relative activities are 13.2 for 5α-cholesten-3-one when the activity of coprostan-3-one is defined as 100.

(c) Optimum pH: 5.2 to 5.7

(d) Stable pH: 4.0 to 7.5

(e) Measurement of titer:

With 0.2 ml of 3 mM coprostan-3-one micelle solution containing 0.33% Triton X-100 is mixed 0.3 ml of a 40 mM Britton-Robinson buffer solution (pH 6.0) containing 0.5% Triton X-100 and 1 mM DTT, and 0.1 ml of a 10 mM NADPH solution, the resulted mixture is added 0.05 ml of an enzyme solution, reacted for 30 minutes at 37° C., and then added 0.1 ml of chloroform to extract sterol and to terminate the reaction. The enzyme solution was mixed with equal amounts of activating fractions and left for 15 minutes at 5° C., then used.

Then, the quantity of coprostanol produced in the reaction solution is determined using TLC/FID iatroscan. The quantity of coprostanol in the reaction solution is determined likewise using an inactivated enzyme which has been previously heated as a control. The enzyme activity which produces 1 μmol of coprostanol per one minute is regarded as 1 unit.

(f) Range of suitable reaction temperature:

In reaction at pH 7.5 for 30 minutes, increasing temperature up to 40° C. is attended by increasing the activity.

(g) Range of temperature stability

After heating treatment at 40° C. for 10 minutes in the presence of 0.5 mM NADPH, it keeps activity of not less than 80% of that before the treatment.

(h) Influence of inhibitor, metal ion:

When 1 mM PCMB, iodine acetamide and EDTA are added and reacted for 30 minutes at pH 7.5 and 37° C., the relative activities are 41, 82 and 101 respectively, if the enzyme activity without adding inhibitor is defined as 100. Further, when the present enzyme is reacted in the presence of 1 mM iron chloride and copper chloride, the relative activities are 12 and 2.7, respectively, in comparison with the case of no addition.

(i) Purification method:

Method 1;

Microbial cells are collected from the culture by centrifugal separation, and the cells are suspended in a 20 mM phosphoric acid-citric acid buffer solution (pH 6.0, containing 0.1 mM DTT). The cells are disrupted by ultrasonication, further, treated with ultrasonication in the presence of 0.2% Triton X-100, solid components are removed by centrifugal separation, to obtain a crude enzyme solution. The crude enzyme solution is dialyzed against a 20 mM PIPES buffer solution (pH 7.5, containing 1 mM DTT, 0.2% Triton X-100, 10% glycerol), then, passed through Blue Sepharose CL-6B (Pharmacia) which has been equilibrated with the same buffer solution, and fractions which have not been adsorbed on Blue Sepharose CL-6B are recovered, and dialyzed against a 20 mM phosphoric acid-citric acid buffer solution (pH 6.0) (containing 0.5 mM NADPH, 1 mM DTT, 0.2% Triton X-100, 10% glycerol). The solution is adsorbed on DEAE-Cellulofine which has been equilibrated with the same buffer solution, then, the buffer solution flows with sodium chloride concentration being increased continuously from 0 to 1.0 M, and active fractions are collected and dialyzed against the buffer solution. The active fractions are adsorbed on Blue Sepharose CL-6B, and fractions which had not been adsorbed were recovered. The fractions which had not been adsorbed were heated at 95° C. for 10 minutes to remove protein and to obtain activating fractions. Then, the active fractions which had been adsorbed on Blue Sepharose were eluted with the same buffer solution containing 1 mM NADPH with sodium chloride concentration being increased continuously from 0 to 1.0 M. To these active fractions, the above-mentioned activating fractions were added to prepare a purified sample.

Method 2;

Microbial cells are collected from the culture by centrifugal separation, and the cells are suspended in a 20 mM phosphoric acid-citric acid buffer solution (pH 6.0, containing 0.1 mM DTT). The cells are disrupted by ultrasonication, further, treated with ultrasonication in the presence of 0.2% Triton X-100, solid components are removed by centrifugal separation, to obtain a crude enzyme solution. The crude enzyme solution is dialyzed against a 20 mM phosphoric acid-citric acid buffer solution (pH 6.0, containing 1 mM DTT, 0.2% Triton X-100, 30% glycerol), then, adsorbed on Blue Sepharose CL-6B (Pharmacia) which has been equilibrated with the same buffer solution. Then, the above-mentioned buffer solution flows with sodium chloride concentration being increased continuously from 0 to 3.0 M, and active fractions are collected. The resulted active fractions are dialyzed against a 20 mM phosphoric acid-citric acid buffer solution B (pH7.5, containing 1mM DTT, 0.2% Triton X-100, 30% glycerol), then adsorbed on DEAE-Cellulofine which has been equilibrated with the same buffer solution B, then, the buffer solution flows with sodium chloride concentration being increased continuously from 0 to 1.0 M, and active fractions are collected and dialyzed against the buffer solution. The active fractions are dialyzed against the same buffer solution B, then adsorbed on Resource Column (Pharmasia). Then, the above-mentioned buffer solution B flows with sodium chloride concentration being increased continuously from 0 to 1.0 M and active fractions are collected to prepare a purified sample.

(j) Coenzyme:

Reduced type β-nicotinamide adenine dinucleotide phosphoric acid (NADPH) is used as a coenzyme.

(k) Molecular weight:

The molecular weight according to SDS polyacrylamide electrophoresis method is about 29,000.

Then, the method for producing the novel cholesterol dehydrogenase B, 4-cholesten-3-one dehydrogenase B and coprostan-3-one dehydrogenase B is described below.

The microorganism used in producing the present enzymes may be any microorganism having the ability to produce the above-mentioned cholesterol dehydrogenase B, 4-cholesten-3-one dehydrogenase B and coprostan-3-one dehydrogenase B, and may also be a variant species or variant strain thereof. As a specific example of the microorganism having the ability to produce the cholesterol dehydrogenase B, 4-cholesten-3-one dehydrogenase B and coprostan-3-one dehydrogenase B and belonging to *Eubacterium,* for example, *Eubacterium* sp. CP 1 is listed.

The above-mentioned *Eubacterium* sp. CP 1 is a strain which has been newly separated from the feces of humans by the present inventors, and mycological properties thereof are as follows.

The present strain exhibits excellent growth by standing culture in a solution under anaerobic conditions at 37° C. using the following basal medium. Tests regarding various properties were investigated under this condition.

Basal medium; 1.2% a bovine brain extracted lipid, 1.8% Trypticase, 0.05% yeast extract, 0.13% dipotassium phosphate, 0.22% sodium chloride, 0.05% cholesterol, 0.04% L-cystine, 0.03% sodium thioglycolate, 0.05% agar, and a small amount of 0.05% Methylene Blue (pH 7.2)

(a) Morphological properties
①  Form of cell; long rod bacterium and grown in the form of chain
②  Size of cell; 0.3 to 0.5 μm×3.0 to 5.0 μm
③  Polymorphism; none
④  Mobility; none
⑤  Spore; none (b) Cultural properties No growth was observed in the bouillon plate agar-media and bouillon broth media under aerobic or anaerobic conditions.

Cultural properties under culturing condition and basal medium in which the present strain can grow are shown below.
①  Basal medium agar plate culture (culturing for 21 days)
   i) Appearance of growth; forming powdery colony
   ii) Color; white
   iii) Gloss; none
   iv) Dispersible pigment; none
②  Basal medium solution culture (culturing for 5 days)
   i) Growth on surface; none
   ii) Turbidity; grows, but, discrimination from sediment in a medium by turbidity is difficult
③  Gelatin stab culture in basal medium
   i) Condition of growth; excellent
   ii) Liquefaction of gelatin; none (C) Physiological properties in basal medium culture
①  Gram staining; positive
②  Reduction of nitrate; negative
③  Litmus milk; coagulation negative
④  Generation of indole; negative
⑤  Generation of hydrogen sulfide; negative
⑥  Hydrolysis of starch; positive
⑦  Decomposition of esculin; positive ⑧ Utilization of an inorganic nitrogen source in a medium which has been obtained by removing trypticase and yeast extract from a basal medium
   i) Nitrate; negative
   ii) Ammonium salt; negative
⑨ Generation of pigment; none
⑩ Urease; negative
⑪ Oxidase; negative
⑫ Catalase; negative
⑬ Growth range
   i) Growth pH range; pH 5 to pH 8 (optimum growth; around pH 7)
   ii) Growth temperature range; 33 to 40° C. (optimum growth temperature; around 34° C.)
⑭ Behavior against oxygen; strictly anaerobic
⑮ O-F test (Hugh Leifson method); negative
⑯ Generation of acid
   i) L-arabinose; acid (small amount)
   ii) D-xylose; acid (observed)
   iii) D-glucose; acid (observed)
   iv) D-mannose; acid (observed)
   v) D-fructose; acid (small amount)
   vi) D-galactose; acid (observed)
   vii) maltose; acid (observed)
   viii) Sucrose; acid (small amount)
   ix) Lactose; acid (observed)
   x) Trehalose; acid (none)
   xi) D-sorbitol; acid (none)
   xii) D-mannitol; acid (none)
   xiii) Inositol; acid (none)
   xiv) Glycerin; acid (none)
   xv) Starch; acid (none)
   xvi) Ribose; acid (observed)
   xvii) Cellobiose; acid (observed)
   xviii) Lactose; acid (observed)
   xix) Melibiose; acid (observed)
   xx) Raffinose; acid (observed)
   xxi) Salicin; acid (observed)
   xxii) Amygdalin; acid (observed)
   xxiii) Melezitose; acid (none)
   xxiv) Glycogen; acid (none)
   xxv) Inulin; acid (none)
   xxvi) Metabolite from saccharides; acetic acid The present strain was gram positive strictly anaerobic long rod bacterium, did not form spores, had no mobility, was negative against all of a catalase, oxydase and urease and formed acids from glucose, and main metabolite thereof was acetic acid. The classificational position of the strain having these mycological properties was compared with description of Bergey's Manual of Systematic Bacteriology vol. 2, 1986, as a result, the strain was identified as a bacterium belonging to *Eubacterium,* and the CP 1 strain was named as *Eubacterium* sp. CP 1. This strain was deposited in the name of FERM BP-5500 to National Institute of Bioscience and Human-Technology Agency of Industrial Science and Technology (Higashi 1-1-3, Tsukuba City, Ibaraki Prefecture, Japan) on Apr. 12, 1996.

As the medium used for culturing a microorganism which produces cholesterol dehydrogenase B, 4-cholesten-3-one dehydrogenase B and coprostan-3-one dehydrogenase B of the present invention, any of the synthetic mediums or natural mediums containing a carbon source, nitrogen source, inorganic substance and the like can be used.

As the carbon source, for example, various carbohydrates can be used such as glucose, maltose, molasses and the like, and the amount used thereof is preferably from 1 to 20 g/L.

As a nitrogen source, for example, ammonium sulfate, ammonium phosphate, ammonium carbonate and ammonium acetate, or nitrogen-containing organic compounds such as peptone, yeast extract, corn steep liquor, casein decomposed material, meat extract, and the like, can be used, and the amount used thereof is preferably from 1 to 20 g/L. The amount of solvent-extract used (chloroform:methanol=2:1) of a bovine brain lipid is preferably from 1 to 20 g/L.

As an inorganic substance, for example, sodium chloride, calcium chloride, magnesium sulfate, potassium monohydrogen phosphate and the like are used, and the amount used thereof is preferably from 0.1 to 2 g/L. The amount used of cystine and sodium thioglycolate is preferably from 0.1 to 1 g/L.

Culturing is conducted under anaerobic conditions by standing culture or stirring culture. Culturing temperature may advantageously be a temperature at which a microorganism grows and produces cholesterol dehydrogenase B, 4-cholesten-3-one dehydrogenase B and coprostan-3-one dehydrogenase B, and preferably from 35 to 40° C. Culturing period varies depending on conditions, and culturing may advantageously be conducted until the maximum amount of these enzymes are produced, usually from about 3 to 10 days.

Cholesterol dehydrogenase B of the present invention that is produced by the CP 1 strain is a novel enzyme, and the physical and chemical properties and method for purification thereof are as follows.

(a) Action: it catalyses the following reaction.
   Cholesterol+NADP→4-cholesten-3-one+NADPH
(b) Substrate specificity
   The present enzyme reacts with steroid having a hydroxyl group at 3β position, and has relative activity of 67, 50 and 39 regarding β sitosterol, campesterol, stigmasterol when the activity of cholesterol is defined as 100.
(c) Optimum pH: 6.7 to 7.7
(d) Stable pH: 5.0 to 10.5
(e) Measurement of titer:
   With 0.2 ml of 3 mM cholesterol micelle solution containing 0.33% Triton X-100 is mixed 0.3 ml of a 50 mM phosphoric acid buffer solution (pH 7.5) containing 1.0% Triton X-100 and 1 mM DTT, and 0.1 ml of a 10 mM NADP solution, to the resulted mixture is added 0.05 ml of an enzyme solution, reacted for 30 minutes at 37° C., and then added 0.1 ml of chloroform to extract sterol and to terminate the reaction.
   Then, the quantity of 4-cholesten-3-one produced in the reaction solution is determined using TLC/FID iatroscan. The quantity of 4-cholesten-3-one produced in the reaction solution is determined likewise using an inactivated enzyme which has been previously heated as a control. The enzyme activity which produces 1 μmol of 4-cholesten-3-one per one minute is regarded as 1 unit.
(f) Range of suitable reaction temperatures:
   In reaction at pH 7.5 for 30 minutes, increasing temperature up to 40° C. is attended by increasing activity.
(g) Range of temperature stability
   After heating treatment at 40° C. for 10 minutes ,it keeps activity of not less than 80% of that before the treatment.
(h) Influence of inhibitor, metal ion:
   When 1 mM PCMB, iodine acetic acid and EDTA are added and reacted for 30 minutes at pH 7.5 and 37° C., the relative activities are 0, 98 and 102 respectively, if the enzyme activity without adding inhibitor is 100. Further, when the present enzyme is reacted in the presence of 1 mM iron chloride and copper chloride, the relative activities are both 0 in comparison to the case of no addition.

(i) Purification method:

Air is bubbled through the culture, and microbial cells adsorbed on the bubble are recovered and concentrated. The concentrated solution is subjected to centrifugal separation to collect the cells, and the cells are suspended in a 20 mM phosphoric acid buffer solution (pH 7.5, containing 1 mM DTT). The cells are disrupted by ultrasonication, further, treated with ultrasonication in the presence of 1.0% Triton X-100, solid components are removed by centrifugal separation, to obtain a crude enzyme solution. To the crude enzyme solution is added 1 mM EDTA, 1 mM iodine acetic acid and 0.5 mM phenylmethylsulfonyl fluoride (PMSF), and the mixture is dialyzed against a 20 mM Tris-hydrochloric acid buffer solution (pH 7.5, containing 1 mM DTT, 10% glycerol, 1 mM EDTA, 1 mM iodine acetic acid, and 0.5 mM PMSF). The crude enzyme solution is adsorbed on Blue Sepharose CL-6B (Pharmacia) which has been equilibrated with the same buffer solution containing 0.25% Triton X-100. Then, lipid components are eluted with the same buffer solution containing 1.0% Triton X-100, then, the above-mentioned buffer solution flows with sodium chloride concentration being increased continuously from 0 to 3.0 M, and active fractions are collected. The resulted active fractions are dialyzed against the above-mentioned buffer solution, then, adsorbed on DEAE-Sepharose Fast Flow which has been equilibrated with the same buffer solution containing 1.0% Triton X-100. Then, the above-mentioned buffer solution flows with sodium chloride concentration being increased continuously from 0 to 0.5 M, and active fractions are collected to obtain a purified sample.

(j) Coenzyme:

β-nicotinamide adenine dinucleotide phosphoric acid (NADP) is used as a coenzyme.

The 4-cholesten-3-one dehydrogenase B of the present invention produced by the CP 1 strain is a novel enzyme, and the physical and chemical properties and method for purification thereof are as follows.

(a) Action: it catalyses the following reaction. 4-cholesten-3-one+NADH→coprostan-3-one+AND (b) Substrate specificity The relative activities are 0 for 5-cholestenon-3-one when the activity of 4-cholesten-3-one is defined as 100.

(c) Optimum pH: 5.3 to 7.0

(d) Stable pH: 5.2 to 8.0

(e) Measurement of titer:

With 0.2 ml of 3 mM 4-cholesten-3-one micelle solution containing 0.33% Triton X-100 is mixed 0.3 ml of a 20 mM Tris-hydrochloric acid buffer solution (pH 7.5) containing 1.0% Triton X-100and 1 mM DTT, and 0.1 ml of a10 mM NADH solution, the resulted mixture is added 0.05 ml of an enzyme solution, reacted for 30 minutes at 37° C., and then added 0.1 ml of chloroform to extract sterol and to terminate the reaction.

Then, the quantity of coprostan-3-one produced in the reaction solution is determined using TLC/FID iatroscan. The quantity of coprostan-3-one produced in the reaction solution is determined likewise using an inactivated enzyme which has been previously heated as a control. The enzyme activity which produces 1 µmol of coprostan-3-one per one minute is regarded as 1 unit.

(f) Range of suitable reaction temperatures:

In reaction at pH 7.5 for 30 minutes, increasing temperature up to 40° C. is attended by increasing the activity.

(g) Range of temperature stability

After heating treatment at 37° C. for 10 minutes, it keeps activity of not less than 80% of that before the treatment.

(h) Influence of inhibitor, metal ion:

When 1 mM PCMB, iodine acetamide and EDTA are added and reacted for 30 minutes at pH 7.5 and 37° C., the relative activities are 0, 99 and 125, respectively, if the enzyme activity without adding inhibitor is 100. Further, when the present enzyme is reacted in the presence of 1 mM iron chloride and copper chloride, the relative activities are 107 and 0, respectively, in comparison with the case of no addition.

(i) Purification method:

Air is bubbled through the culture, and microbial cells adsorbed on the bubble are recovered and concentrated. The concentrated solution is subjected to centrifugal separation to collect the cells, and the cells are suspended in a 20 mM phosphoric acid buffer solution (pH 7.5, containing 1 mM DTT). The cells are disrupted by ultrasonication, further, treated with ultrasonication in the presence of 1.0% Triton X-100, solid components are removed by centrifugal separation, to obtain a crude enzyme solution. To the crude enzyme solution is added 1 mM EDTA, 1 mM iodine acetic acid and 0.5 mM PMSF, and the mixture was dialyzed against a 20 mM Tris-hydrochloric acid buffer solution (pH 7.5, containing 1 mM DTT, 10% glycerol, 1 mM EDTA, 1 mM iodine acetic acid, and 0.5 mM PMSF). The enzyme solution is adsorbed on Blue Sepharose CL-6B (Pharmacia) which has been equilibrated with the same buffer solution containing 0.25% Triton X-100. Then, lipid components are eluted with the same buffer solution containing 1.0% Triton X-100, then, the above-mentioned buffer solution flows with sodium chloride concentration being increased continuously from 0 to 3.0 M, and active fractions are collected. The resulted active fractions are dialyzed against the above-mentioned buffer solution, then, adsorbed on DEAE-Sepharose Fast Flow which has been equilibrated with the same buffer solution containing 1.0% Triton X-100. Then, the above-mentioned buffer solution flows with sodium chloride concentration being increased continuously from 0 to 0.5M, and active fractions are collected to obtain a purified sample.

(j) Coenzyme:

Reduced type β-nicotinamide adenine dinucleotide (NADH) is used as a coenzyme.

The coprostan-3-one dehydrogenase B of the present invention produced by the CP 1 strain is a novel enzyme, and the physical and chemical properties and method for purification thereof are as follows.

(a) Action: it catalyses the following reaction. coprostan-3-one+NADPH→coprostanol+NADP (b) Substrate specificity The relative activities are 0 for 5α-cholesten-3-one when the activity of coprostan-3-one is defined as 100.

(c) Optimum pH: 5.4 to 7.6

(d) Stable pH: 4.5 to 7.0

(e) Measurement of titer:

With 0.2 ml of 3 mM coprostan-3-one micelle solution containing 0.33% Triton X-100 is mixed 0.3 ml of a 20 mM Tris-hydrochloric acid buffer solution (pH 7.5) containing 1.0% Triton X-100 and 1 mM DTT, and 0.1 ml of a 10 mM NADPH solution, to the resulted mixture is added 0.05 ml of an enzyme solution, reacted for 30 minutes at 37° C., and then added 0.1 ml of chloroform to extract sterol and to terminate the reaction.

Then, the quantity of coprostanol produced in the reaction solution is determined using TLC/FID iatroscan. The quantity of coprostanol in the reaction solution is determined likewise using an inactivated enzyme which has been previously heated as a control. The enzyme activity which produces 1 µmol of coprostanol per one minute is regarded as 1 unit.

(f) Range of suitable reaction temperature:

In reaction at pH 7.5 for 30 minutes, increasing temperature up to 45° C. is attended by increasing the activity.

(g) Range of temperature stability

After heating treatment at 45° C. for 10 minutes, it keeps activity of not less than 80% of that before the treatment.

(h) Influence of inhibitor, metal ion:

When 1 mM PCMB, iodine acetamide and EDTA are added and reacted for 30 minutes at pH 7.5 and 37° C., the relative activities are 0, 95 and 112, respectively, if the enzyme activity without adding inhibitor is 100. Further, when the present enzyme is reacted in the presence of 1 mM iron chloride and copper chloride, the relative activities are 105 and 0, respectively, in comparison to the case of no addition.

(i) Purification method:

Air is bubbled through the culture, and microbial cells adsorbed on the bubbles are recovered and concentrated. The concentrated solution is subjected to centrifugal separation to collect the cells, and the cells are suspended in a 20 mM phosphoric acid buffer solution (pH 7.5, containing 1 mM DTT). The cells are disrupted by ultrasonication, further, treated with ultrasonication in the presence of 1.0% Triton X-100, solid components are removed by centrifugal separation, to obtain a crude enzyme solution. To the crude enzyme solution is added 1 mM EDTA, 1 mM iodine acetic acid and 0.5 mM PMSF, and the mixture is dialyzed against a 20 mM Tris-hydrochloric acid buffer solution (pH 7.5, containing 1 mM DTT, 10% glycerol, 1 mM EDTA, 1 mM iodine acetic acid, and 0.5 mM PMSF). The crude enzyme solution is adsorbed on Blue Sepharose CL-6B (Pharmacia) which has been equilibrated with the same buffer solution containing 0.25% Triton X-100. Then, lipid components are eluted with the same buffer solution containing 1.0% Triton X-100, then, the above-mentioned buffer solution flows with sodium chloride concentration being increased continuously from 0 to 3.0 M, and active fractions are collected. The resulting active fractions are dialyzed against the above-mentioned buffer solution, then, adsorbed on DEAE-Sepharose Fast Flow which has been equilibrated with the same buffer solution containing 1.0% Triton X-100. Then, the above-mentioned buffer solution flows with sodium chloride concentration being increased continuously from 0 to 0.5 M, and active fractions are collected to obtain a purified sample.

(j) Coenzyme:

Reduced type β-nicotinamide adenine dinucleotide phosphoric acid (NADPH) is used as a coenzyme.

As the cholesterol-reduced composition of the present invention, microbial cells or treated materials thereof, crude purified enzymes, purified enzymes and the like containing these three enzymes may be used without any treatment provided they have activities of a cholesterol dehydrogenase, 4-cholesten-3-one dehydrogenase and coprostan-3-one dehydrogenase, and further, those in the form of tablets, powders, fine particles, granules, capsules, syrups and the like molded with vehicles which are acceptable for food or medicine may be used. The composition of the present invention may be added as a composition to be added into food or feed for reducing the amount of cholesterol in the food or feed, or may be orally administered via oral route for reducing the cholesterol level in serum. When a crude purified enzyme or purified enzyme is used as the composition of the present invention, the composition optionally may be advantageously prepared so that nicotinamide, phosphate ion or phospholipase is contained in the composition. Examples of the form of the oral composition of the present invention include tablets, powders, fine particles, granules, capsules, syrups, enteric agent, troches and the like. In the case of addition or administration, as the vehicle, any compound such as saccharides like sorbitol, lactose, glucose, lactose, dextrin, starch, crystalline cellulose and the like; inorganic compounds like calcium carbonate, calcium sulfate and the like; distilled water, sesame oil, corn oil, olive oil, cotton seed oil and the like, generally can be used. In preparing the composition, additives such as binder, lubricant, disperser, suspending agent, emulsifying agent, diluent, buffering agent, antioxidant, bacterium inhibiting agent and the like may be used.

The amount to be added may be advantageously controlled to be the above-mentioned value necessary for the enzymatic conversion or the microbial conversion in the method for producing a cholesterol-reduced substance of the present invention.

The dosage varies depending on age, sex, administration pattern, times of administration, form and the like, and regarding dosage for oral administration for adults, it is suitable that the amount of bacteria is $1 \times 10^7$ to $1 \times 10^{12}$ cell/day, preferably $1 \times 10^8$ to $1 \times 10^{11}$ cell/day and the amount of three enzymes is 10 to $1 \times 10^5$ unit/day, preferably $1 \times 10^2$ to $1 \times 10^4$ unit/day, and that the composition is divided into 1 to 4 portions for one day-administration. If necessary, dosage out of the above-mentioned restriction can also be adopted.

BEST MODE FOR CARRYING OUT THE INVENTION

Figure 1:
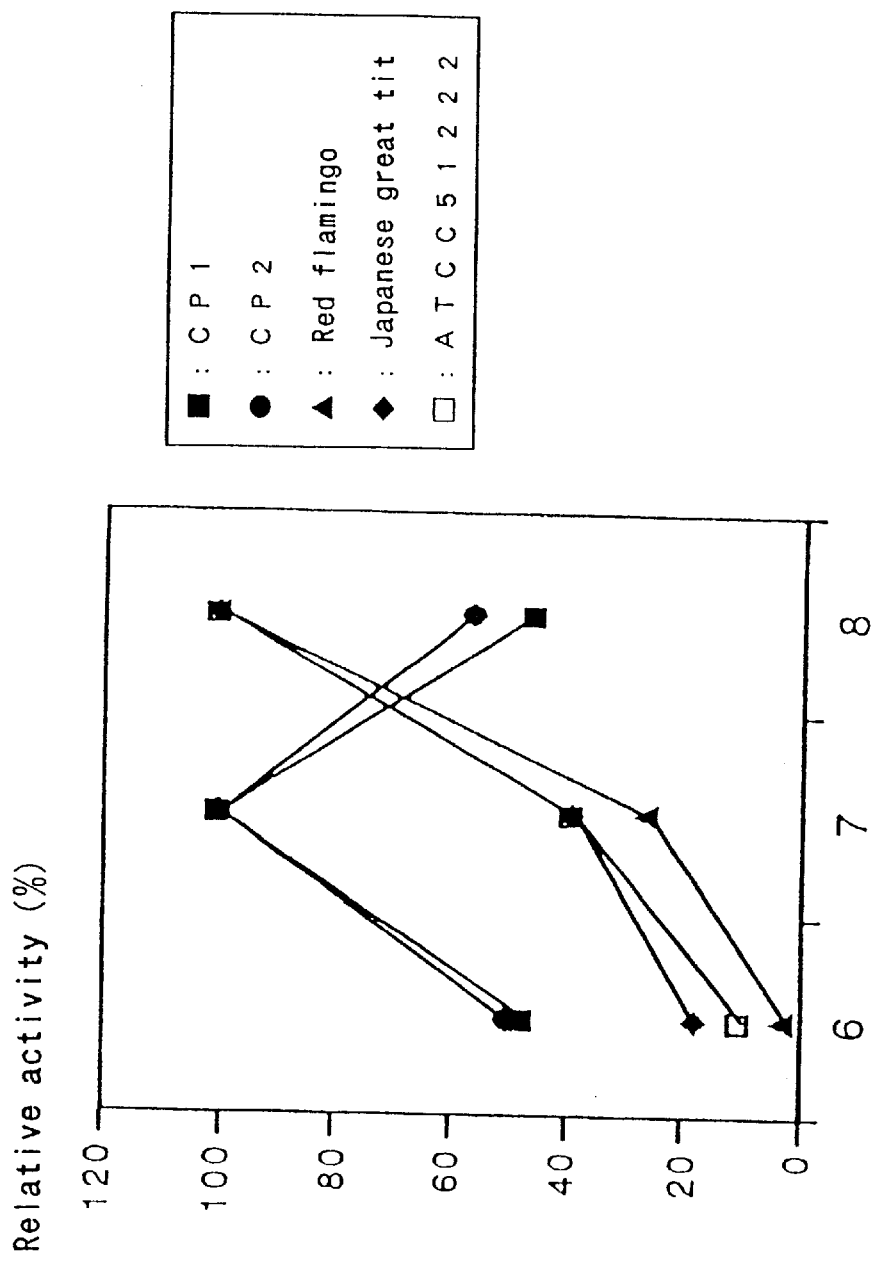
FIG. 1 is a graph showing results of measurement of conversion enzyme activity at pH 6, 7 and 8 of various cholesterol dehydrogenases derived from microorganisms.

The following embodiments and comparative embodiments further illustrate the characteristics of the present invention, but, do not limit the scope thereof. In all embodiments, all parts are by weight unless otherwise stated.

Embodiment 1 (screening of cholesterol reducing conversion enzyme producing microorganism)

The present inventors have screened various microorganisms such as stock microorganisms mainly including 300 kinds (species level) of actinomycetes, fungi and bacteria, aerobic bacteria separated from 100 kinds of various soils, and anaerobic bacteria from 7 feces samples of humans, 8 feces samples of mammals other than humans and 9 feces samples of birds, to find a cholesterol reducing conversion enzyme group having optimum pH in neutral pH range.

As a result, cholesterol reducing conversion enzymatic activity has been detected which converts cholesterol to coprostanol in anaerobic microorganisms separated from feces, as shown below.

Each feces was separately poured on to 6 kinds of media for detection (see, Table 1) to which cholesterol had been added as a substrate, and reducing conversion enzymatic activity of cultured substance, namely, whether coprostanol had been generated from cholesterol or not was investigated. The results are shown in Tables 2 to 4. In Table 1, CHOL represents cholesterol and PL represents phospholipid, respectively.

Formulations of nutrition media are as follows. Nutrition medium 1:

1.8% trypticase, 0.05% yeast extract, 0.13% dipotassium phosphate, 0.22% sodium chloride, 0.04% L-cystine, 0.03% sodium thioglycolate, 0.05% agar (pH 7.2) Nutrition medium 2:

1.0% casitone, 1.0% yeast extract, 0.5% lactose, 0.5% sodium pyruvate, 0.05% sodium thioglycolate (pH 7.5) Nutrition medium 3:

0.24% Lab-lemco powder (Oxoid), 1.0% proteose peptone, 0.5% yeast extract, 0.4% disodium phosphate, 0.15% glucose, 0.05% soluble starch, 0.02% cystine, 0.05% cysteine hydrochloride (pH 7.6 to 7.8)

TABLE 1

| No. | | Additive | | |
|---|---|---|---|---|
| ① | Nutrition medium 1 | | +1.2% bovine brain lipid | |
| ② | Nutrition medium 1 | | +1.2% bovine brain lipid | +5% soybean oil |
| ③ | Nutrition medium 2 | +0.2% CHOL +0.1% PL | | |
| ④ | Nutrition medium 2 | +0.2% CHOL +0.1% PL | +1.2% bovine brain lipid | |
| ⑤ | Nutrition medium 3 | | | +5% horse blood |
| ⑥ | Nutrition medium 3 | | +1.2% bovine brain lipid | +5% horse blood |

TABLE 2

| | | Medium No. | | | | | |
|---|---|---|---|---|---|---|---|
| No. | Mammal | ① | ② | ③ | ④ | ⑤ | ⑥ |
| 1 | Bear | | | | | | |
| 2 | Giraffe | | | | | | |
| 3 | Zebra | | | | | | |
| 4 | Elephant | | | | | | |
| 5 | Lion | | | | + | | |
| 6 | Cheetah | | | | | | |
| 7 | Koala | | | | | | |
| 8 | Tapir | | | | | | |

TABLE 3

| No. | Human | ① | ② | ③ | ④ | ⑤ | ⑥ |
|---|---|---|---|---|---|---|---|
| 1 | Human 1 | + | | | | | |
| 2 | Human 2 | | | | | | |
| 3 | Human 3 | | | | | | |
| 4 | Human 4 | | | | | | |
| 5 | Human 5 | | | | | | |
| 6 | Human 6 | | | | | | |
| 7 | Human 7 | | | | | | |

TABLE 4

| No. | Bird | ① | ② | ③ | ④ | ⑤ | ⑥ |
|---|---|---|---|---|---|---|---|
| 1 | Ostrich | | | | | | |
| 2 | Crane | | | | | | |
| 3 | Emu | | | | | | |
| 4 | Pheasant | | | | | | |
| 5 | Flamingo | | | + | | | |
| 6 | Japanese crested ibis | | | | | | |
| 7 | Red-crested white crane | | | | | | |
| 8 | Japanese great tit | | + | | | | |
| 9 | Peacock | | | | | | |

As can be seen from Tables 2 to 4, growth of microorganisms having reducing conversion enzymatic activity was detected from cultivated materials in 4 kinds of feces of human sample 1 (nutrition medium 1), lion (nutrition medium 4), red flamingo (nutrition medium 3) and Japanese great tit (nutrition medium 2), and the enzymatic activity could not be detected from feces samples 2 to 7 of humans, feces samples of mammals other than lion such as bear, giraffe and the like, and feces samples of birds other than flamingo and Japanese great tit such as ostrich, crane and the like. As described above, reducing conversion enzymatic activity could be detected from specific feces of specific kinds of animals, and in addition, only in specific media.

Embodiments 2 (selection of an enzyme having optimum pH in neutral pH range)

The culture in 4 kinds of feces of human sample 1, lion, red flamingo and Japanese great tit in which conversion activity from cholesterol to coprostanol was detected, and a culture of a bacterium belonging to *Eubacterium* ATCC 51222 described in the above-mentioned Beitz, et al., Applied Microbiology and Biotechnology 43, 887 (1995), were, respectively, treated with ultrasonication to disrupt the bacterial cells (*Eubacterium* species ATCC 21408 described in Beitz, et al., U.S. Pat. No. 4,921,710 could not be obtained from ATCC). Conversion active fractions in this disrupted cells were adsorbed on Blue Sepharose and eluted, cholesterol dehydrogenase active fractions were investigated in the cholesterol conversion system, and the activity was measured at pH 6, pH 7 and pH 8, and the results are shown in FIG. 1.

As is known also from FIG. 1, cholesterol dehydrogenase A from the CP 2 strain derived from lion and cholesterol dehydrogenase B from the CP 1 strain derived from human sample 1 exhibited maximum activity at near pH 7 which is in neutral pH range and other samples exhibited maximum activity at near pH 8 which is in alkaline pH range. Thus, a cholesterol dehydrogenase having an optimum pH in neutral pH range has not been known yet until now, therefore, it is a novel enzyme.

Embodiment 3 (production of cells of *Eubacterium* sp. CP 2)

20 g of casitone (Difco), 20 g of yeast extract (Difco), 10 g of soluble starch, 10 g of sodium pyruvate, 1 g of sodium thioglycolate, 1 g of potassium chloride and 0.2 g of lecithin (type 4S, Sigma) were dissolved in 2 L of de-ionized water, pH thereof was controlled at 7.5, and the solution was poured into 3 liter Erlenmeyer flasks, separately. This medium was sterilized at 120° C. for 15 minutes, then, the CP 2 strain was inoculated, and standing culture in anaerobic condition was conducted at a temperature of 37° C. for 7 days. After completion of the culture, 8.5 g of a precipitate was obtained from 2 L of the culture by centrifugal separation, and the precipitate was used as cells-containing material.

Embodiment 4 (production of extracted material from cells of *Eubacterium* sp. CP 2)

The cells-containing material obtained in Embodiment 3 was suspended in 30 ml of 40 mM Britton-Robinson buffer solution (pH 6.5), and the cells suspension was treated with an ultrasonication at 60 W for 10 minutes, to obtain extracted material from the cells.

Embodiment 5 (production of cholesterol dehydrogenase A)

The extracted material obtained in Embodiment 4 was treated with ultrasonicaion for 30 seconds in the presence of 1 mM DTT and 0.2% Triton X-100, and then solid components were removed by centrifugal separation to obtain a crude enzyme solution. The crude enzyme solution was dialyzed against a 20 mM PIPES buffer solution (pH 7.5, containing 1 mM DTT, 0.2% Triton X-100 and 10% glycerol), then, adsorbed on Blue Sepharose CL-6B (Pharmacia) equilibrated with the buffer solution. Then, the buffer solution was flown with sodium chloride concentration being increased continuously from 0 to 3.0 M, and active fractions were collected. The resulted active fractions were dialyzed against the afore-said buffer solution, then, adsorbed on Red Sepharose CL-6B (Pharmacia). Then, the above-mentioned buffer solution was flown with sodium chloride concentration being increased continuously from 0 to 3.0 M, and active fractions were collected to prepare a purified sample. The specific activity of this purified sample was 4.49 unit/mg protein, and the yield thereof was 37.4%.

This purified sample was subjected to SDS polyacrylamide gel electrophoresis, and dyed by using a silver staining kit (Daiichi Kagaku K.K.), and a single band was recognized in the position of molecular weight of about 58,800.

Comparative Embodiment 1 (optimum pH of cholesterol dehydrogenase)

ATCC 51222 strain and CP 2 strain was inoculated to the medium described in Embodiment 3, respectively, and standing culture in anaerobic condition was conducted at a temperature of 37° C. for 7 days. After completion of the culture, cells-containing material was obtained from the culture solution by centrifugal separation, and this cells-containing material was suspended in 50 ml of 40 mM Britton-Robinson buffer solution (pH 6.5), and the cell suspension was treated with an ultrasonication at 60 W for 10 minutes, to obtain extracted material from cells. A purified sample of cholesterol dehydrogenase was obtained according to the method described in Embodiment 3 from this extracted material.

Figure 2:
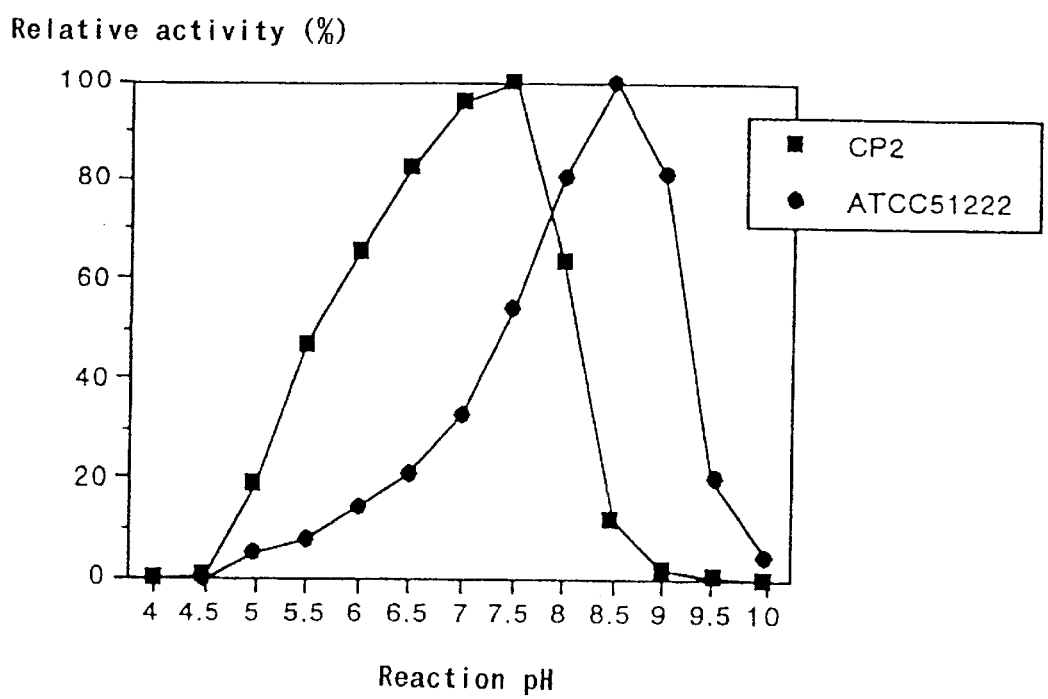
FIG. 2 is a graph showing results of measurement of optimum pH of cholesterol dehydrogenases derived from a CP 2 strain and ATCC 51222 strain belonging to *Eubacterium*.

The relative activities of these enzymes at various pH values are shown in FIG. 2. As is known from FIG. 2, the cholesterol dehydrogenase of the CP 2 strain having an optimum pH in a neutral side corresponding to pH of meat, egg and milk is more excellent in food treatment than the cholesterol dehydrogenase of ATCC 51222 strain having optimum pH in alkaline side.

Embodiment 6 (production of 4-cholesten-3-one dehydrogenase A)

The extracted material obtained in Embodiment 4 was treated with ultrasonication for 30 seconds in the presence of 1 mM DTT and 0.2% Triton X-100, and solid components were removed by centrifugal separation to obtain a crude enzyme solution. The crude enzyme solution was dialyzed against a 20 mM PIPES buffer solution (pH 7.5, containing 1 mM DTT, 0.2% Triton X-100 and 10% glycerol), then, adsorbed on Blue Sepharose CL-6B (Pharmacia) equilibrated with the buffer solution. Then, the buffer solution was flown with sodium chloride concentration being increased continuously from 0 to 3.0 M, and active fractions were collected. The resulted active fractions were dialyzed against the afore-said buffer solution, then, adsorbed on Resource Column (Pharmacia). Then, the above-mentioned buffer solution was flown with sodium chloride concentration being increased continuously from 0 to 1.0 M, and active fractions were collected to prepare a purified sample. The specific activity of this purified sample was 3.31 unit/mg protein, and the yield thereof was 40.1%.

This purified sample was subjected to SDS polyacrylamide gel electrophoresis, and dyed by using a silver staining kit (Daiichi Kagaku K.K.), and a single band was recognized in the position of molecular weight of about 37,500.

Embodiment 7 (production of coprostan-3-one dehydrogenase A)

The extracted material obtained in Embodiment 4 was treated with ultrasonication for 30 seconds in the presence of 1 mM DTT and 0.2% Triton X-100, and solid components were removed by centrifugal separation to obtain a crude enzyme solution. The crude enzyme solution was dialyzed against a 20 mM PIPES buffer solution (pH 7.5, containing 1 mM DTT, 0.2% Triton X-100 and 10% glycerol), then, passed through Blue Sepharose CL-6B (Pharmacia) equilibrated with the buffer solution, fractions which had not been adsorbed on Blue Sepharose CL-6B were recovered, and dialyzed against 20 mM phosphoric acid-citric acid buffer solution (pH 6.0) (containing 0.5 mM NADPH, 1 mM DTT, 0.2% Triton X-100 and 10% glycerol). The enzyme solution was adsorbed on DEAE-Cellulofine equilibrated with the buffer solution, then, the buffer solution was flown with sodium chloride concentration being increased continuously from 0 to 1.0 M, and active fractions were collected, then, dialyzed against the afore-said buffer solution, then, the active components were adsorbed on Blue Sepharose CL-6B, and non-adsorbed fractions were recovered. The non-adsorbed fractions were heated for 10 minutes at 95° C. to remove protein to prepare activating fractions. Then, elution was conducted using the above-mentioned buffer solution containing 1 mM NADPH with sodium chloride concentration being increased continuously from 0 to 3.0 M, and active fractions were collected, and above-mentioned activating fractions were added to prepare a purified sample. The specific activity of this purified sample was 4.51 unit/mg protein, and the yield thereof was 19.0%.

Embodiment 8 (production of coprostan-3-one dehydrogenase A)

The cells-containing material obtained in Embodiment 3 was suspended in 30 ml of a 20 mM phosphoric acid-citric acid buffer solution (pH 6.0, 1 mM DTT) and the cells suspension was treated by an ultrasonicator (BRANSON SONIFIER Model. 250) for 5 minutes at 120 W, to obtain extracted material from the cells. This extracted material was treated with ultrasonication for 30 seconds in the presence of 1 mM DTT and 0.2% Triton X-100, and solid components were removed by centrifugal separation to obtain a crude enzyme solution. The crude enzyme solution was dialyzed against 20 mM phosphoric acid-citric acid buffer solution A (pH 6.0, containing 1 mM DTT, 0.2% Triton X-100 and 30% glycerol), then, adsorbed on Blue Sepharose CL-6B (Pharmacia) equilibrated with the buffer solution, then, the above-mentioned buffer solution was flown with sodium chloride concentration being increased continuously from 0 to 3.0 M, and active fractions were collected. The resulted active fractions were dialyzed against 20 mM phosphoric acid-citric acid buffer solution B (pH 7.5, containing 1 mM DTT, 0.2% Triton X-100 and 30% glycerol), then, adsorbed on DEAE-Cellulofine equilibrated with the buffer solution B, then, the above-mentioned buffer solution was flown with sodium chloride concentration being increased continuously from 0 to 1.0 M, active fractions were collected and dialyzed against the same buffer solution. The resulting active fractions were dialyzed against the same buffer solution B, then, adsorbed on Resource Column (Pharmacia). Then, the buffer solution B was flown with sodium chloride concentration being increased continuously from 0 to 1.0 M, and active fractions were collected to prepare a purified sample. The specific activity of this purified sample was 4.90 unit/mg protein, and the yield thereof was 9.5%.

This purified sample was subjected to SDS polyacrylamide gel electrophoresis, and dyed by using a silver staining kit (Daiichi Kagaku K.K.), and a single band was recognized in the position of molecular weight of about 29,000.

Embodiment 9 (optimum pH of enzyme system from CP 2 strain derived from lion)

Figure 3:
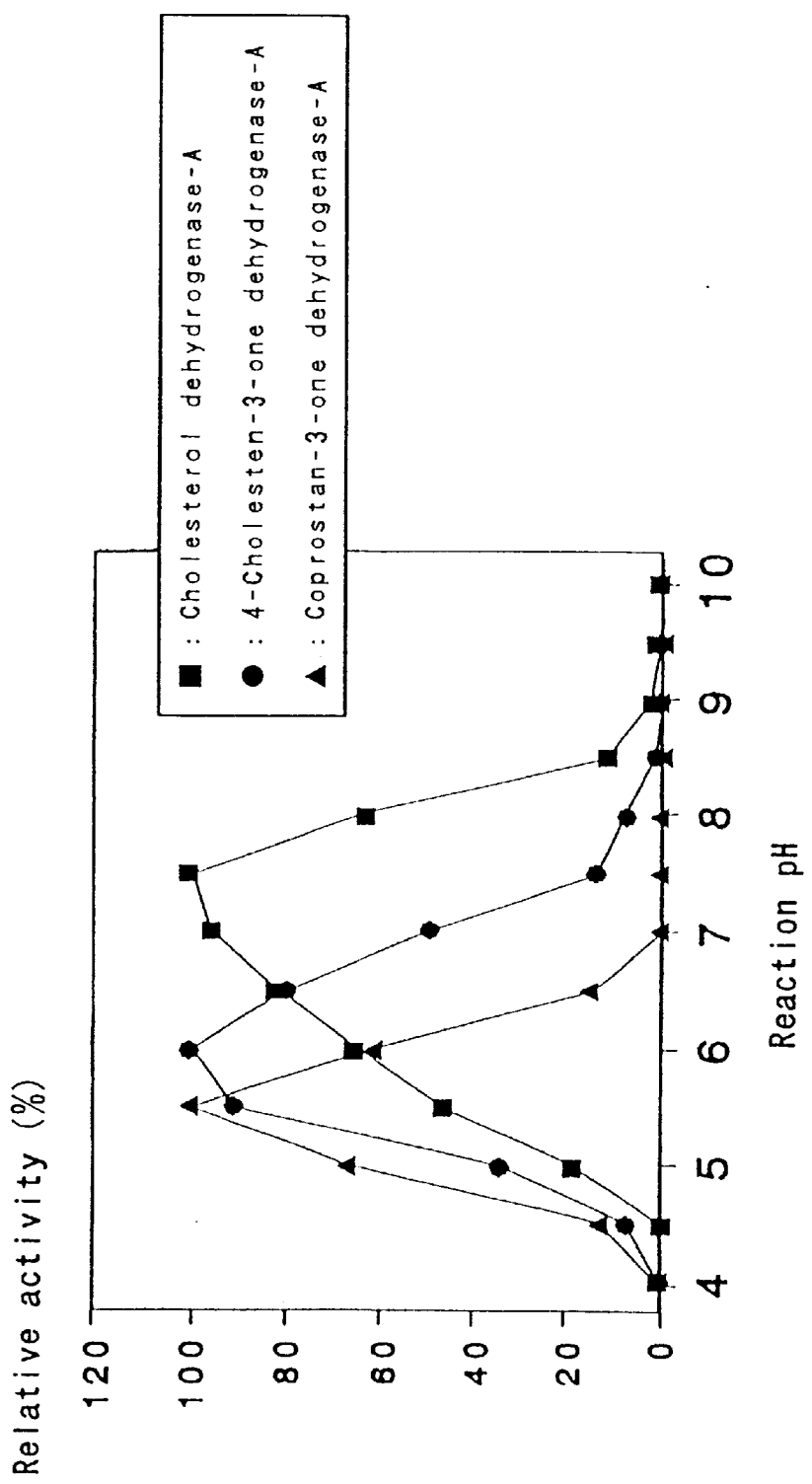
FIG. 3 is a graph showing results of measurement of optimum pH of cholesterol dehydrogenase A, 4-cholesten-3-one dehydrogenase A and coprostan-3-one dehydrogenase A.

Now, it will be shown that an enzyme system from the CP 2 derived from lion is particularly excellent in meat treatment. This enzyme system has optimum pH for reducing sequentially from cholesterol dehydrogenase through 4-cholesten-3-one dehydrogenase to coprostan-3-one dehydrogenase. And the optimum pH of cholesterol dehydrogenase is in a neutral range, and the optimum pH values of 4-cholesten-3-one dehydrogenase and coprostan-3-one dehydrogenase are within the pH range from 5.5 to 6.5 which is a weak acidic range corresponding to the pH of meat. Therefore, when meat treatment is conducted using this enzyme system, cholesterol in meat can be continuously converted to coprostanol without stock of intermediates such as 4-cholesten-3-one and coprostan-3-one. The measurement results of the optimum pH values of these enzymes are shown in FIG. 3.

Embodiment 10 (enzymatic conversion to coprostanol in aging period of meat)

10 g of beef 6 hours after slaughtering was made into minced meat, and to this was added the cholesterol dehydrogenase obtained in Embodiment 5 (0.2 unit/g meat), the 4-cholesten-3-one dehydrogenase obtained in Embodiment 6 (0.2 unit/g meat) and the coprostan-3-one dehydrogenase obtained in Embodiment 7 (0.2 unit/g meat) and mixed, and the mixture was aged at 5° C. for 7 days. Also, mixtures to which 0.5 ml of a 20% aqueous nicotinamide solution had been further added, meat to which phospholipase (2 unit/g meat) had been further added and meat to which both of them had been further added at the mixing were aged at 50° C. for 7 days, respectively.

After aging, the meat was freeze-dried and lipid components were extracted with a 25 ml extraction solvent (chloroform:methanol=2:1). Regarding the resulting extracted sample, the amount of converted sterol products was determined using gas chromatography (manufactured by GL Science, TC-1701, column φ0.25 μm×30 m). The conversion ratio of cholesterol to coprostanol in the meat was measured, and the results are shown in Table 5. In Table 5, PL-D represents phospholipase D and COP represents coprostanol, respectively.

As can be seen from Table 5, conversion to coprostanol could not be observed when only a conversion enzyme was added, and the conversion increased synergistically when nicotinamide was added or when both nicotinamide and phospholipase D were added.

TABLE 5

| Treating type | COP conversion (%) |
| --- | --- |
| No addition | 0 |
| Enzyme | 0 |
| Enzyme + PL-D | 0.84 |
| Nicotinamide | 0 |
| Enzyme + nicotinamide | 4.4 |
| Enzyme + PL-D + nicotinamide | 49.1 |

Embodiment 11 (enzymatic conversion to coprostanol in processing meat)

10 g of beef 6 hours after slaughtering was made into minced meat, and further homogenated. To this homogenated meat was added and mixed the cells-extracted material described in Embodiment 4, and the mixture was heated at 37° C. for 2 hours. The amounts to be added were 0.2 unit/g meat for cholesterol dehydrogenase A, 0.4 unit/g meat for 4-cholesten-3-one dehydrogenase A and 0.4 unit/g meat for coprostan-3-one dehydrogenase A. Also, a mixture to which 0.5 ml of a 20% aqueous nicotinamide solution had been further added at the mixing was processed similarly.

After completion of the processing, the conversion ratio to coprostanol in the resulted sample was measured according to the method in Embodiment 10. The conversion ratio of cholesterol to coprostanol in the resulting meat was measured, and the results are shown in Table 6.

As is known also from Table 6, enzymatic conversion of cholesterol to coprostanol in meat could be recognized only with addition of an enzyme source. When nicotinamide was added, the conversion ratio further increased.

TABLE 6

| meat treating type | COP conversion (%) |
| --- | --- |
| No addition | 0 |
| Enzyme | 12.1 |
| Enzyme + nicotinamide | 51.5 |

Embodiment 12 (microbial conversion of cholesterol in processing meet)

10 g of commercially available beef was processed into meat paste by a food cutter, then, to this was added 0.57 g of cells of the CP 2 strain described in Embodiment 3. This mixture was fermented at 37° C. for 20 hours to obtain processed meat. After completion of the processing, the conversion ratio to coprostanol in the resulting sample was measured according to the method in Embodiment 10. The conversion ratio of cholesterol to coprostanol in the resulting meat was 82.3%.

Embodiment 13 (microbial conversion of cholesterol in milk)

To 10 ml of commercially available milk was added 0.42 g of cells of the CP 2 strain described in Embodiment 3, and this mixture was fermented at 37° C. for 20 hours to obtain processed milk. After completion of the processing, the conversion ratio to coprostanol in the resulting sample was measured according to the method in Embodiment 10. The conversion ratio of cholesterol to coprostanol in the resulting meat was 64.4%.

Embodiment 14 (microbial conversion of cholesterol in egg)

With 10 ml of a 10% aqueous yolk solution was mixed 0.42 g of cells of the CP 2 strain described in Embodiment 3, and this mixture was fermented at 37° C. for 20 hours to obtain a processed egg. After completion of the processing, the conversion ratio to coprostanol in the resulting sample was measured according to the method in Embodiment 10. The conversion ratio of cholesterol to coprostanol in the resulting egg was 27.8%.

Embodiment 15 (Production of cells of *Eubacterium* sp. CP 1)

Commercially available bovine brain was homogenated and freeze-dried, and extracted three times with a 3-fold amount of extraction solvent (chloroform methanol =2), then, the solvent was removed to obtain a lipid extract. The yield was 51.9% in terms of dry weight.

48 g of this bovine brain lipid extract, 72 g of trypticase (BBL), 2 g of yeast extract (Difco), 8.8 g of sodium chloride, 5.2 g of dipotassium hydrogen phosphate, 2 g of Bacto Agar (Difco), 1.6 g of L-cystine, 2 g of cholesterol, 1.2 g of sodium thioglycolate were dissolved in 4 L of de-ionized water, and pH of the solution was controlled to 7.2, and poured into two 3-L Erlenmeyer flasks separately. This medium was sterilized at 120° C. for 15 minutes, then, a CP 1 strain was inoculated, and stirring culture in anaerobic condition was conducted at 37° C. for 5 days.

Figure 4:
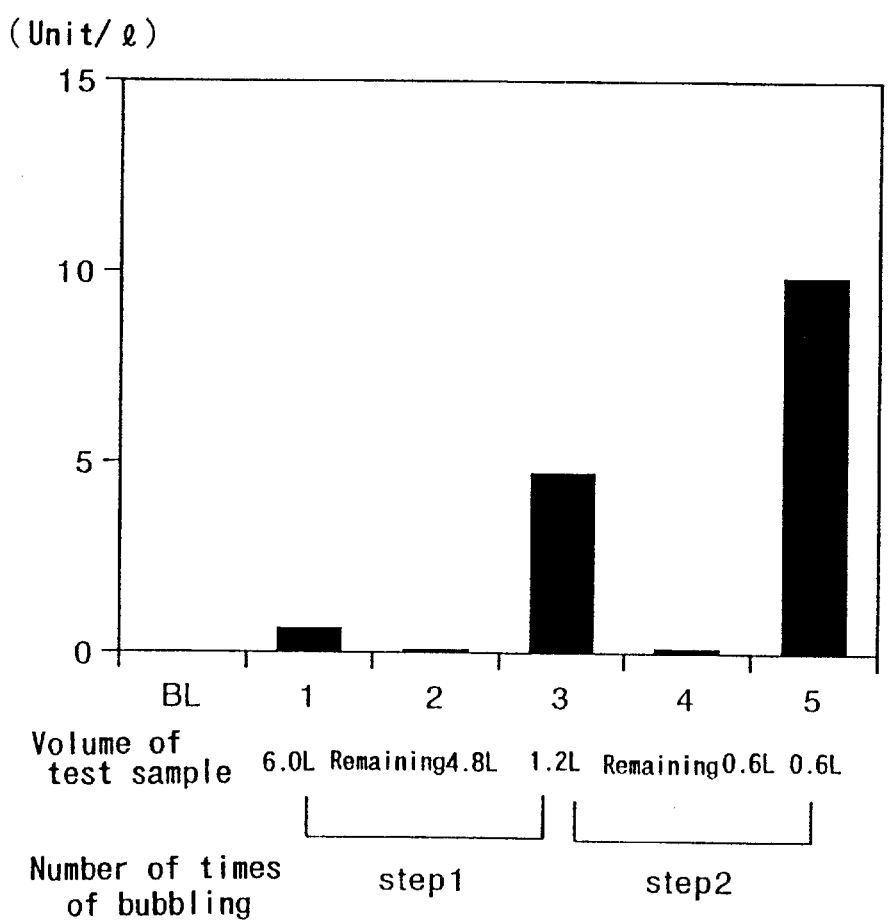
FIG. 4 is a graph showing progress of concentration of a CP 1 strain belonging to *Eubacterium* and concentration of coprostanol in a medium according to a bubbling method.

The recovering of cells of the CP 1 strain from the culture was conducted by centrifugal separation which is an ordinary method of recovering microbial cells. However, the CP 1 strain was adsorbed on an insoluble lipid and coagulated, the specific gravity thereof decreased and the strain became inhomogeneous. Therefore, the cells could not be recovered. Because it was suggested that the surface of the cells was hydrophobic and since the cells were adsorbed on an insoluble lipid, the cells were adsorbed on hydrophobic air by a bubbling method and recovered. Namely, air was bubbled in from the lower side of the culture filled into a column, and a part of the bubble on which the cells concentrated was recovered from the upper end of the column. This operation was repeated several times for obtaining a cells-concentrate. Whether the cells-concentrate was obtained or not was recognized by measuring the activity of 4-cholesten-3-one dehydrogenase B in the extracted material which was obtained by treating a sample solution taken from the bubble part and a remaining sample solution after recovering the bubble part by an ultrasonicator at 60 W for 10 minutes. The results when the bubbling was conducted twice are shown in FIG. 4. From FIG. 4, it is known that the bubbling method is effective for recovering cells of the CP 1 strain.

Embodiment 16 (production of cholesterol dehydrogenase B, 4-cholesten-3-one dehydrogenase B and coprostan-3-one dehydrogenase B by *Eubacterium* sp. CP 1 strain)

The cells-concentrate obtained in Embodiment 15 is centrifugally separated, the resulting cells are suspended in a 20 mM Tris-hydrochloric acid buffer solution (pH 7.5, containing 1 mM dithiothreitol). The cells are disrupted by ultrasonication, further, treated with ultrasonication in the presence of 1.0% Triton X-100, then, solid components are removed by centrifugal separation, to obtain a crude enzyme solution. To the crude enzyme solution is added 1 mM EDTA, 1 mM iodine acetic acid and 0.5 mM PMSF, and the mixture is dialyzed against a 20 mM Tris-hycrochloric acid buffer solution (pH 7.5, containing 1 mM dithiothreitol, 10% glycerol, 1 mM EDTA, 1 mM iodine actic acid, 0.5 mM PMSF). The crude enzyme solution was diluted to a 4-fold volume with the same buffer solution, then, adsorbed on Blue Sepharose CL-6B (Pharmacia) which has been equilibrated with the same buffer solution containing 0.25% Triton X-100. Then, lipid components are eluted with the same buffer solution containing 1.0% Triton X-100, then, the above-mentioned buffer solution flows with sodium chloride concentration being increased continuously from 0 to 3.0 M, and active fractions are collected. The resulting active fractions are dialyzed against the above-mentioned buffer solution, then, adsorbed on Resource (Pharmacia) which has been equilibrated with the same buffer solution containing 1.0% Triton X-100. Then, the above-mentioned buffer solution flows with sodium chloride concentration increased continuously from 0 to 0.5 M, and active fractions are collected to prepare a purified product.

Figure 5:
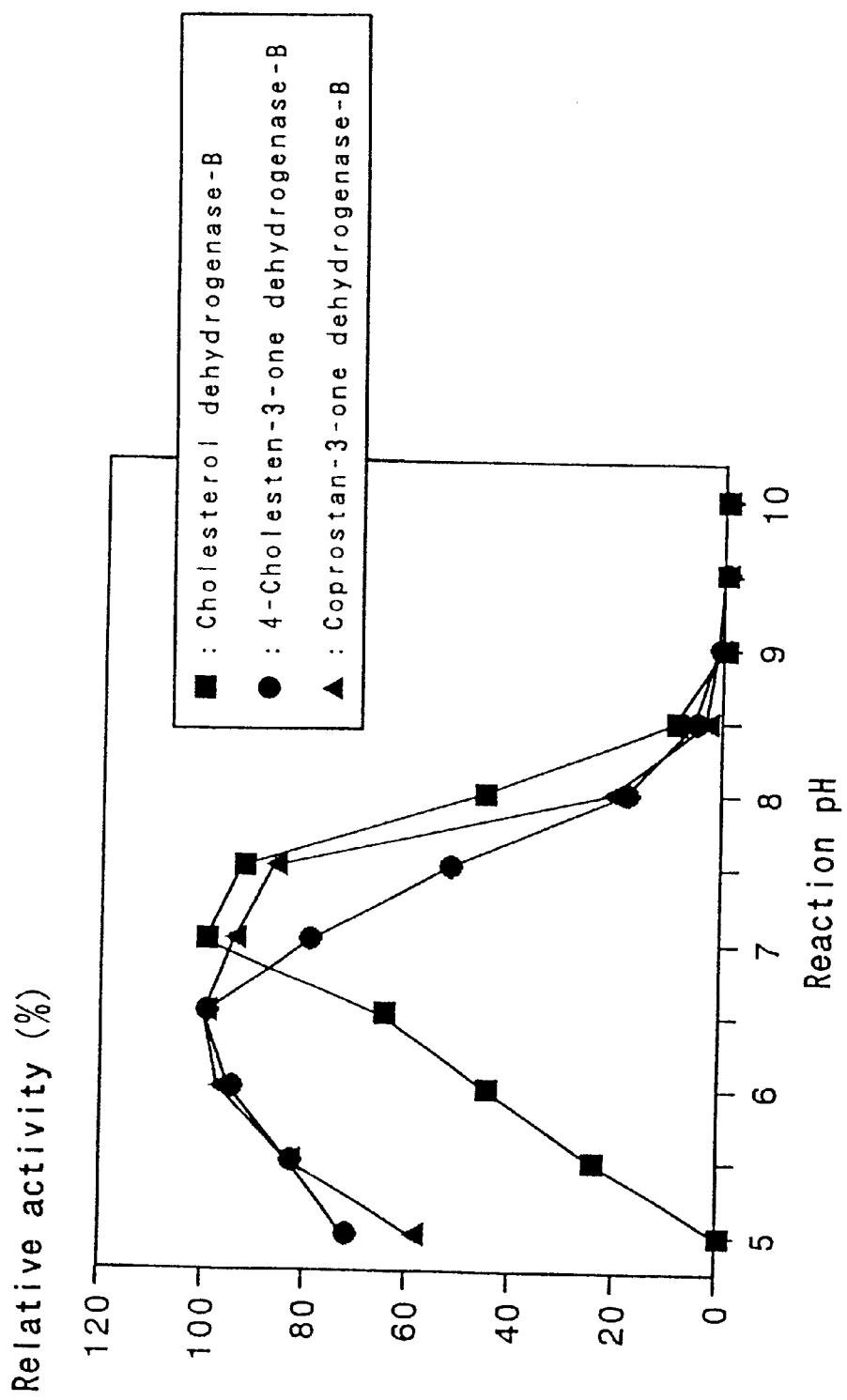
FIG. 5 is a graph showing results of measurement of optimum pH of cholesterol dehydrogenase B, 4-cholesten-3-one dehydrogenase B and coprostan-3-one dehydrogenase B.

In this purified product, the specific activity of cholesterol dehydrogenase B was 0.116 unit/mg protein, and the yield thereof was 32.1%, the specific activity of 4-cholesten-3-one dehydrogenase B was 1.24 unit/mg protein, and the yield thereof was 65.2%, and the specific activity of coprostan-3-one dehydrogenase B was 0.835 unit/mg protein, and the yield thereof was 54.8%. The results of measurement of optimum pH values of these enzymes are shown in FIG. 5.

Embodiment 17 (activation of cholesterol dehydrogenase B by phosphoric acid)

Figure 6:
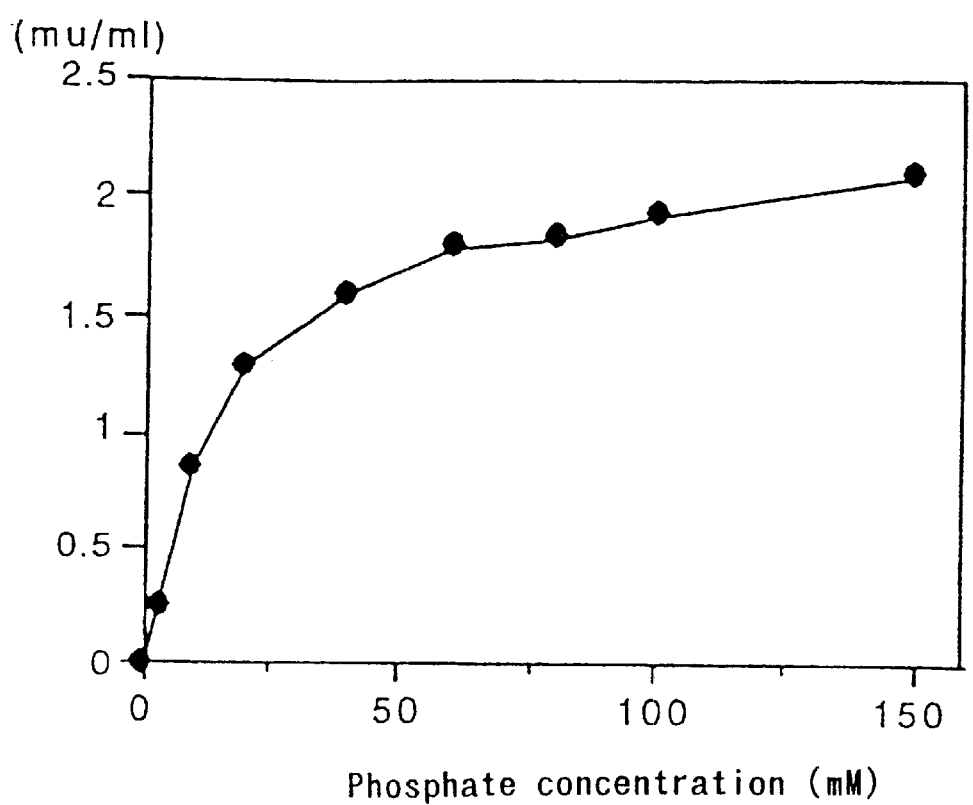
FIG. 6 is a graph showing results of measurement of enzymatic conversion activity of cholesterol dehydrogenase B when a phosphate ion is added.

Conversion reaction by cholesterol dehydrogenase B is remarkably activated by a phosphate ion. As the phosphate ion source, sodium polyphosphate, sodium metaphosphate, sodium pyrophosphate, trisodium phosphate and the like can be used, and the results when trisodium phosphate was used are shown in FIG. 6. From this, it is known that addition of a phosphate ion is desirable in conversion of cholesterol to coprostanol using cholesterol dehydrogenase B.

Embodiment 18 (enzymatic conversion of cholesterol in meat using enzymes of *Eubacterium* sp. CP 1)

10 g of beef 6 hours after slaughtering was made into minced meat, and to this was added each enzyme described in Embodiment 15 and 0.05 g of sodium phosphate, and the mixture was heated at 37° C. for 2 hours. The amounts to be added were 0.2 unit/g meat for cholesterol dehydrogenase B, 0.2 unit/g meat for 4-cholesten-3-one dehydrogenase B and 0.2 unit/g meat for coprostan-3-one dehydrogenase B. Also, a mixture to which 0.5 ml of a 20% aqueous nicotinamide solution had been further added at the mixing was processed similarly.

After completion of the processing, the conversion ratio to coprostanol in the resulting sample was measured according to the method in Embodiment 10. The conversion ratio of cholesterol to coprostanol in the resulted meat was measured, and the results are shown in Table 7. As can be seen also from Table 7, enzymatic conversion ratio of cholesterol to coprostanol in meat could be recognized only with addition of enzymes. When nicotinamide was added, the conversion ratio was further increased.

TABLE 7

| Meat treating type | COP conversion (%) |
|---|---|
| No addition | 0 |
| Cell extract | 28.1 |
| Cell extract + nicotinamide | 68.1 |

Embodiments 19

Tablets (300 mg per one tablet) are produced by the usual method according to the following formulation.

| | |
|---|---|
| Dried cells of the CP 1 strain ($1 \times 10^{10}$ cells) | 10 mg |
| Lactose | 230 mg |
| Corn Starch | 30 mg |
| Synthetic aluminum silicate | 12 mg |

| -continued | |
|---|---|
| Carboxymethylcellulose calcium | 15 mg |
| Magnesium stearate | 3 mg |

Embodiments 20

Tablets (300 mg per one tablet) are produced by the usual method according to the following formulation.

| | |
|---|---|
| Dried cells of the CP 2 strain (1 × $10^{10}$ cells) | 10 mg |
| Lactose | 190 mg |
| Corn Starch | 70 mg |
| Synthetic aluminum silicate | 12 mg |
| Carboxymethylcellulose calcium | 15 mg |
| Magnesium stearate | 3 mg |

Embodiments 21

Hard capsules (700 mg per one capsule) are produced according to the following formulation.

| | |
|---|---|
| Cholesterol dehydrogenase A (purified sample described in Embodiment 5) | 100 mg |
| 4-Cholesten-3-one dehydrogenase A (purified sample described in Embodiment 6) | 150 mg |
| Coprostan-3-one dehydrogenase A (purified sample described in Embodiment 8) | 100 mg |
| Lactose | 230 mg |
| Corn Starch | 100 mg |
| Hydroxypropylcellulose | 20 mg |

To 100 mg of cholesterol dehydrogenase A and 100 mg of coprostan-3-one dehydrogenase A, respectively, and 150 mg of 4-cholesten-3-one dehydrogenase A are added 230 mg of lactose and 100 mg of corn starch and mixed, to this mixture is added an aqueous solution of 20 mg of hydroxypropycellulose and kneaded. Then, granules are produced by an ordinary method using an extrusion granulator. These granules are filled in a gelatin hard capsule to produce a hard capsule.

Embodiments 22

Powders (1000 mg per one piece) are produced by an ordinary method according to the following formulation.

| | |
|---|---|
| Cholesterol dehydrogenase B (purified sample described in Embodiment 15) | 100 mg |
| 4-Cholesten-3-one dehydrogenase B (purified sample described in Embodiment 15) | 150 mg |
| Coprostan-3-one dehydrogenase B (purified sample described in Embodiment 15) | 100 mg |
| Nicotinamide | 50 mg |

| -continued | |
|---|---|
| Lactose | 430 mg |
| Corn Starch | 170 mg |

INDUSTRIAL APPLICABILITY

According to the present invention, cholesterol concentration can be reduced by converting cholesterol in a substance selectively to coprostanol having low intestinal tract absorbability without losing the property and condition of the cholesterol-containing substance such as meat and the like.

Further, the cholesterol level in serum can be reduced by orally administrating a composition of microbial cells-containing the novel enzyme of the present invention and converting cholesterol to coprostanol in the small intestine to inhibit absorption of the cholesterol.

What is claimed is:

1. A process for producing a cholesterol-reduced substance, wherein cholesterol in a cholesterol-containing substance is treated with microbial cells containing cholesterol dehydrogenase, 4-cholesten-3-one dehydrogenase and coprostan-3-one dehydrogenase for converting the cholesterol to coprostanol, to reduce the amount of cholesterol, and wherein said cholesterol dehydrogenase has its optimum pH in the neutral pH range.

2. The process for producing a cholesterol-reduced substance according to claim 1, wherein said microbial cells are cells of Eubacterium sp. CP1(FERM BP-5500) or Eubacterium sp. CP2(FERM BP-5501).

3. The method for reducing the amount of cholesterol according to claim 1, wherein said microbial cells are cells of a microorganism belonging to Eubacterium.

4. A method for reducing the amount of cholesterol, wherein cholesterol in a cholesterol-containing substance is treated with microbial cells containing cholesterol dehydrogenase, 4-cholesten-3-one dehydrogenase and coprostan-3-one dehydrogenase for converting the cholesterol to coprostanol, to reduce the amount of cholesterol, and wherein said cholesterol dehydrogenase has its optimum pH in the neutral pH range.

5. The process for producing a cholesterol-reduced substance according to claim 4, wherein said microbial cells are cells of a microorganism belonging to Eubacterium.

6. The method for reducing the amount of cholesterol according to claim 4, wherein said microbial cells are cells of Eubacterium sp. CP1(FERM BP-5500) or Eubacterium sp. CP2(FERM BP-5501).

\* \* \* \* \*